United States Patent
Li

(10) Patent No.: US 11,459,584 B2
(45) Date of Patent: Oct. 4, 2022

(54) GENE SEQUENCE OF RECOMBINANT HUMAN TYPE II MITOCHONDRIAL DYNEIN-LIKE GTPASE AND USES THEREOF

(71) Applicant: WUHAN NEUROPHTH BIOTECHNOLOGY LIMITED COMPANY, Hubei (CN)

(72) Inventor: Bin Li, Hubei (CN)

(73) Assignee: Wuhan Neurophth Biotechnology Limited Company, Hubei (CN)

( * ) Notice: Subject to any disclaimer, the term of this patent is extended or adjusted under 35 U.S.C. 154(b) by 150 days.

(21) Appl. No.: 17/182,903

(22) Filed: Feb. 23, 2021

(65) Prior Publication Data
US 2021/0180086 A1    Jun. 17, 2021

Related U.S. Application Data

(63) Continuation of application No. PCT/CN2019/102352, filed on Aug. 23, 2019.

(30) Foreign Application Priority Data

Aug. 23, 2018    (CN) .......................... 201810968173.0

(51) Int. Cl.
| | | |
|---|---|---|
| C12N 15/86 | (2006.01) | |
| A61K 38/46 | (2006.01) | |
| A61K 48/00 | (2006.01) | |

(52) U.S. Cl.
CPC .............. *C12N 15/86* (2013.01); *A61K 38/46* (2013.01); *A61K 48/00* (2013.01); *C12Y 306/05005* (2013.01); *C12N 2750/14141* (2013.01); *C12N 2800/22* (2013.01); *C12Y 306/00* (2013.01)

(58) Field of Classification Search
CPC ............ C12Y 306/05005; C12N 15/85; C12N 15/86; C12N 2800/22; A61K 48/00–48/0091; A61P 27/02
See application file for complete search history.

(56) References Cited

U.S. PATENT DOCUMENTS

| | | |
|---|---|---|
| 4,797,368 A | 1/1989 | Carter et al. |
| 5,139,941 A | 8/1992 | Muzyczka et al. |
| 6,566,118 B1 | 5/2003 | Atkinson et al. |
| 6,596,535 B1 | 7/2003 | Carter |
| 6,989,264 B2 | 1/2006 | Atkinson et al. |
| 6,995,006 B2 | 2/2006 | Atkinson et al. |

FOREIGN PATENT DOCUMENTS

| | | |
|---|---|---|
| CN | 105358568 A | 2/2016 |
| EP | 0488528 B1 | 10/1991 |
| WO | WO 91/18088 A1 | 11/1991 |
| WO | WO 93/09239 A1 | 5/1993 |
| WO | WO 2006/073496 A2 | 7/2006 |
| WO | WO 2007/134818 A2 | 11/2007 |
| WO | WO 2018/102672 A1 | 6/2018 |
| WO | WO 2020/038473 | 2/2020 |

OTHER PUBLICATIONS

NM_015560.2, publicly available Jul. 2018, printed as pp. 1/7-7/7. (Year: 2018).*
Chapter 2. Understanding Epidemiology of Vision Loss and Impairment in the United States in Making Eye Health a Population Health Imperative. Welp A, Woodbury RB, McCoy MA, et al., editors. Washington (DC): National Academies Press (US); Sep. 15, 2016, printed as pp. 1/82-82/82. (Year: 2016).*
Newman et al. Hereditary optic neuropathies. Eye, vol. 18, pp. 1144-1160, 2004. (Year: 2004).*
La Morgia et al. Medical management of hereditary optic neuropathies. Frontiers in Neurology, vol. 5, Article 141, Jul. 2014, printed as pp. 1-7. (Year: 2014).*
Del Dotto et al. OPA1: How much do we known to approach therapy? Pharmacological Research, vol. 131, pp. 199-210, Feb. 15, 2018. (Year: 2018).*
Awwad et al. Principles of pharmacology in the eye. British Journal of Pharmacology, vol. 174, pp. 4205-4223, 2017. (Year: 2017).*
Oliviera et al. Non-viral strategies for ocular gene delivery. Materials Science and Engineering, vol. 77, pp. 1275-1289, Apr. 18, 2017. (Year: 2017).*
Rogdrigues et al. Pharmaceutical development of AAV-based gene therapy products for the eye. Pharmaceutical Research, vol. 36, Article 29, published online Dec. 27, 2018, printed as pp. 1/20-20/20. (Year: 2018).*
Formichi, et al. "Analysis of opa1 isoforms expression and apoptosis regulation in autosomal dominant optic atrophy (ADOA) patients with mutations in the opa1 gene." Journal of the Neurological Sciences, Mar. 6, 2015, 351(1-2):99-108, DOI: 10.1016/j.jns.2015.02.047.
NCBI Reference Sequence: NM_130831.2. *Homo sapiens* OPA1 mitochondrial dynamin like GTPase (OPA1), transcript variant 2, mRNA. May 28, 2019.

(Continued)

*Primary Examiner* — Jennifer Dunston
(74) *Attorney, Agent, or Firm* — Cooley LLP

(57) ABSTRACT

A gene sequence of recombinant human type II mitochondrial dynein-like GTPase having a nucleotide sequence shown in SEQ ID NO: 1 and uses thereof. A fusion nucleic acid comprising a nucleic acid encoding human type II mitochondrial dynein-like GTPase. A recombinant expression vector comprising the nucleic acid or a fusion nucleic acid. A transformant by which the nucleic acid or the fusion nucleic acid is introduced into a host. A non-human mammalian ADOA model based on the inactivation of the gene of type II mitochondrial dynein-like GTPase, which can effectively improve the pathological manifestations of ADOA using a recombinant expression vector encoding the human type II mitochondrial dynein-like GTPase. The expression level of the nucleic acid encoding the human type II mitochondrial dynein-like GTPase is higher, therefore, more human type II mitochondrial dynein-like GTPase can be obtained in the mitochondria. which can better treat eye diseases such as ADOA.

24 Claims, 11 Drawing Sheets

Specification includes a Sequence Listing.

(56) References Cited

OTHER PUBLICATIONS

Zhang, et al. "Research Progress on Autosomal Dominant Optic Atrophy." Intl. Rev. of Opthal 30(3): 206-209 (2006), and English Abstract.

* cited by examiner

```
  1  ATGTGGCGCCTGCGCCGCGCCGCCGTGGCCTGCGAGGTGTGCCAGAGCCTGGTGAAGCAC
     ||||||||| ||  |  |||||||| ||||||| ||||||||| || ||| ||||| |||
  1  ATGTGGCGACTACGTCGGGCCGCTGTGGCCTGTGAGGTCTGCCAGTCTTTAGTGAAACAC

61  AGCAGCGGCATCAAGGGCAGCCTGCCCCTGCAGAAGCTGCACCTGGTGAGCCGCAGCATC
     |||| |||||| |||  || | ||| |||||||| ||| | |||| || ||   ||
 61  AGCTCTGGAATAAAAGGAAGTTTACCACTACAAAAACTACATCTGGTTTCACGAAGCATT

121  TACCACAGCCACCACCCCACCCTGAAGCTGCAGCGCCCCAGCTGCGCACCAGCTTCCAG
     | |||||| ||||||| || ||||||||| |  |    ||    | |||| ||| |||
121  TATCATTCACATCATCCTACCTTAAAGCTTCAACGACCCCAATTAAGGACATCCTTTCAG

181  CAGTTCAGCAGCCTGACCAACCTGCCCCTGCGCAAGCTGAAGTTCAGCCCCATCAAGTAC
     ||||| | |  ||||| |||| |  |||| |  |||||||| |||||     | |  | |
181  CAGTTCTCTTCTCTGACAAACCTTCCTTTACGTAAACTGAAATTCTCTCCAATTAAATAT

241  GGCTACCAGCCCCGCCGCAACTTCTGGCCCGCCCGCCTGGCCACCCGCCTGCTGAAGCTG
     |||||||||||  |||  ||  ||| ||||  |  | | |||||  | |||| |||| |
241  GGCTACCAGCCTCGCAGGAATTTTTGGCCAGCAAGATTAGCTACGAGACTCTTAAAACTT

301  CGCTACCTGATCCTGGGCAGCGCCGTGGGCGGCGGCTACACCGCCAAGAAGACCTTCGAC
     ||||| || || || |||||  | ||||| ||||||||||| ||||| |||||| |||
301  CGCTATCTCATACTAGGATCGGCTGTTGGGGGTGGCTACACAGCCAAAAAGACTTTTGAT

361  CAGTGGAAGGACATGATCCCCGACCTGAGCGAGTACAAGTGGATCGTGCCCGACATCGTG
     ||||||||  |||||||| || |||| ||  ||||| ||||||| ||||| ||||| |||
361  CAGTGGAAAGATATGATACCGGACCTTAGTGAATATAAATGGATTGTGCCTGACATTGTG

421  TGGGAGATCGACGAGTACATCGACTTCGGCAGCCCCGAGGAGACCGCCTTCCGCGCCACC
     ||||| || || ||| ||||||  || || |  ||| ||||   | || || ||| |
421  TGGGAAATTGATGAGTATATCGATTTTGGTTCTCCGGAAGAAACGGCGTTTAGAGCAACA

481  GACCGCGGCAGCGAGAGCGACAAGCACTTCCGCAAGGTGAGCGACAAGGAGAAGATCGAC
     || || || |  |||| ||||||||| || ||||||| ||| |||||||| |||| |||
481  GATCGTGGATCTGAAAGTGACAAGCATTTTAGAAAGGTGTCAGACAAAGAGAAAATTGAC

541  CAGCTGCAGGAGGAGCTGCTGCACACCCAGCTGAAGTACCAGCGCATCCTGGAGCGCCTG
     ||  || |||| ||| ||||||||| ||| |||| ||| ||| | ||  || |  | |
541  CAACTTCAGGAAGAACTTCTGCACACTCAGTTGAAGTATCAGAGAATCTTGGAACGATTA

601  GAGAAGGAGAACAAGGAGCTGCGCAAGCTGGTGCTGCAGAAGGACGACAAGGGCATCCAC
     ||  |||||||||| || |||   ||   | ||| ||||| || |||||  | ||  |
601  GAAAAGGAGAACAAAGAATTGAGAAAATTAGTATTGCAGAAAGATGACAAAGCATTCAT

661  CACCGCAAGCTGAAGAAGAGCCTGATCGACATGTACAGCGAGGTGCTGGACGTGCTGAGC
     || |  ||||| ||||| || || ||  ||||||| | |||||| || |  |||| | |
661  CATAGAAAGCTTAAGAAATCTTTGATTGACATGTATTCTGAAGTTCTTGATGTTCTCTCT

721  GACTACGACGCCAGCTACAACACCCAGGACCACCTGCCCCGCGTGGTGGTGGGCGAC
     ||  | || || ||| || || || || || ||| |||| ||| || ||| ||||
721  GATTATGATGCCAGTTATAATACGCAAGATCATCTGCCACGGGTTGTTGTGGTTGGAGAT

781  CAGAGCGCCGGCAAGACCAGCGTGCTGGAGATGATCGCCCAGGCCCGCATCTTCCCCCGC
     |||||||| |  |||||| || ||||| | | ||| |||| | |||  | |||||| |
781  CAGAGTGCTGGAAAGACTAGTGTGTTGGAAATGATTGCCCAAGCTCGAATATTCCCAAGA

841  GGCAGCGGCGAGATGATGACCCGCAGCCCCGTGAAGGTGACCCTGAGCGAGGGCCCCCAC
     |||  || | ||||||||||| | || || ||||||||||| |||||||||||| || |
841  GGATCTGGGGAGATGATGACACGTTCTCCAGTTAAGGTGACTCTGAGTGAAGGTCCTCAC

901  CACGTGGCCCTGTTCAAGGACAGCAGCCGCGAGTTCGACCTGACCAAGGAGGAGGACCTG
     || |||||| ||||  ||| || || | |||||| |||| ||| |||||||||| | |
901  CATGTGGCCCTATATTAAAGATAGTTCTCGGGAGTTTGATCTTACCAAAGAAGAAGATCTT

961  GCCGCCCTGCGCCACGAGATCGAGCTGCGCATGCGCAAGAACGTGAAGGAGGGCTGCACC
     ||  |  || ||||| ||  |||||| | |||| ||||||| | |||||| |||| | |
961  GCAGCATTAAGACATGAAATAGAACTTCGAATGAGGAAAAATGTGAAAGAAGGCTGTACC
```

Fig. 1

```
1021  GTGAGCCCCGAGACCATCAGCCTGAACGTGAAGGGCCCCGGCCTGCAGCGCATGGTGCTG
      |  | |||||||||||| | ||| || ||||  || ||||| |||| | |||||||||| |
1021  GTTAGCCCTGAGACCATATCCTTAAATGTAAAAGGCCCTGGACTACAGAGGATGGTGCTT

1081  GTGGACCTGCCCGGCGTGATCAACACCGTGACCAGCGGCATGGCCCCCGACACCAAGGAG
      || ||| | ||| |||||| |  ||| ||||||   |||||| ||||||||||||| ||
1081  GTTGACTTACCAGGTGTGATTAATACTGTGACATCAGGCATGGCTCCTGACACAAAGGAA

1141  ACCATCTTCAGCATCAGCAAGGCCTACATGCAGAACCCCAACGCCATCATCCTGTGCATC
      || ||| |||| ||||||||||| ||||||||||| || || |||||||| |||| |  
1141  ACTATTTTCAGTATCAGCAAAGCTTACATGCAGAATCCTAATGCCATCATACTGTGTATT

1201  CAGGACGGCAGCGTGGACGCCGAGCGCAGCATCGTGACCGACCTGGTGAGCCAGATGGAC
      || || | |||   ||| ||||  |||| |||||| ||  |  || |||||| |||||||
1201  CAAGATGGATCTGTGGATGCTGAACGCAGTATTGTTACAGACTTGGTCAGTCAAATGGAC

1261  CCCCACGGCCGCCGCACCATCTTCGTGCTGACCAAGGTGGACCTGGCCGAGAAGAACGTG
      ||   |||  |   |||||| | |  |||||||| |||||| |||||||||||| || | 
1261  CCTCATGGAAGGAGAACCATATTCGTTTTGACCAAAGTAGACCTGGCAGAGAAAAATGTA

1321  GCCAGCCCCAGCCGCATCCAGCAGATCATCGAGGGCAAGCTGTTCCCCATGAAGGCCCTG
      ||||| || ||| |  |||||||||||| ||||| |||||| ||||| |||||||| | |
1321  GCCAGTCCAAGCAGGATTCAGCAGATAATTGAAGGAAAGCTCTTCCCAATGAAGCTTTA

1381  GGCTACTTCGCCGTGGTGACCGGCAAGGGCAACAGCAGCGAGAGCATCGAGGCCATCCGC
      || || ||  | |||||| |||  ||||  ||||| ||||| || |||||| | | || |
1381  GGTTATTTTGCTGTTGTAACAGGAAAAGGGAACAGCTCTGAAAGCATTGAAGCTATAAGA

1441  GAGTACGAGGAGGAGTTCTTCCAGAACAGCAAGCTGCTGAAGACCAGCATGCTGAAGGCC
      ||  | |||||| ||||| ||||| |||||||||| || |||||||  ||||| |||| |
1441  GAATATGAAGAAGAGTTTTTTCAGAATTCAAAGCTCCTAAAGACAAGCATGCTAAAGGCA

1501  CACCAGGTGACCACCCGCAACCTGAGCCTGGCCGTGAGCGACTGCTTCTGGAAGATGGTG
      ||||| ||||| || ||||  |||||| ||||||| || | |||| || |||||||||||
1501  CACCAAGTGACTACAAGAAATTTAAGCCTTGCAGTATCAGACTGCTTTTGGAAAATGGTA

1561  CGCGAGAGCGTGGAGCAGCAGGCCGACAGCTTCAAGGCCACCCGCTTCAACCTGGAGACC
      || ||||| ||| || || |||||||  | |||||||| ||| | ||| || |||| | |
1561  CGAGAGTCTGTTGAACAACAGGCTGATAGTTTCAAAGCAACACGTTTTAACCTTGAAACT

1621  GAGTGGAAGAACAACTACCCCCGCCTGCGCGAGCTGGACCGCAACGAGCTGTTCGAGAAG
      ||  |||||||| || |||||| ||||||  |  |||| ||||| || ||||| |||| |
1621  GAATGGAAGAATAACTATCCTCGCCTGCGGGAACTTGACCGGAATGAACTATTTGAAAAA

1681  GCCAAGAACGAGATCCTGGACGAGGTGATCAGCCTGAGCCAGGTGACCCCCAAGCACTGG
      ||  | || ||||||||  || ||||  || ||||||||||||| |||| ||| ||||| 
1681  GCTAAAAATGAAATCCTTGATGAAGTTATCAGTCTGAGCCAGGTTACACCAAAACATTGG

1741  GAGGAGATCCTGCAGCAGAGCCTGTGGGAGCGCGTGAGCACCCACGTGATCGAGAACATC
      ||||| ||||| || ||  | ||||||| ||   || ||| | ||||| || |||||||| 
1741  GAGGAAATCCTTCAACAATCTTTGTGGGAAAGAGTATCAACTCATGTGATTGAAAACATC

1801  TACCTGCCCGCCGCCCAGACCATGAACAGCGGCACCTTCAACACCACCGTGGACATCAAG
      |||||  || || || |||||||||| |||||||| ||||| ||||||||||| ||||| 
1801  TACCTTCCAGCTGCGCAGACCATGAATTCAGGAACTTTTAACACCACAGTGGATATCAAG

1861  CTGAAGCAGTGGACCGACAAGCAGCTGCCCAACAAGGCCGTGGAGGTGGCCTGGGAGACC
      || || ||||||||  |  | || ||||| ||  | ||  || |||| || ||||||||||
1861  CTTAAACAGTGGACTGATAAACAACTTCCTAATAAAGCAGTAGAGGTTGCTTGGGAGACC

1921  CTGCAGGAGGAGTTCAGCCGCTTCATGACCGAGCCCAAGGGCAAGGAGCACGACGACATC
      || || ||  ||||  ||  |||| ||||| |||  || |  ||||||||| || |||| 
1921  CTACAAGAAGAATTTTCCCGCTTTATGACAGAACCGAAAGGAAAGAGCATGATGACATA

1981  TTCGACAAGCTGAAGGAGGCCGTGAAGGAGGAGAGCATCAAGCGCCACAAGTGGAACGAC
      || ||||| || |||||||  |||||||| ||||| |||||| ||||| ||||||| || 
1981  TTTGATAAACTTAAAGAGGCTGTTAAGGAAGAAAGTATTAAACGACACAAGTGGAATGAC
```

Fig. 1 (continued)

```
2041 TTCGCCGAGGACAGCCTGCGCGTGATCCAGCACAACGCCCTGGAGGACCGCAGCATCAGC
     |||  | ||||||||||| | ||  ||  || ||| || ||||||||||| |   || |
2041 TTTGCGGAGGACAGCTTGAGGGTTATTCAACACAATGCTTTGGAAGACCGATCCATATCT

2101 GACAAGCAGCAGTGGGACGCCGCCATCTACTTCATGGAGGAGGCCCTGCAGGCCCGCCTG
     || ||||||||  ||||  |  ||||  |||  |||||||| |||||||||| |  |||
2101 GATAAACAGCAATGGGATGCAGCTATTTATTTTATGGAAGAGGCTCTGCAGGCTCGTCTC

2161 AAGGACACCGAGAACGCCATCGAGAACATGGTGGGCCCCGACTGGAAGAAGCGCTGGCTG
     ||||| || || || || || ||||  ||||||| || ||||||||| | |  |||  |
2161 AAGGATACTGAAAATGCAATTGAAAACATGGTGGGTCCAGACTGGAAAAAGAGGTGGTTA

2221 TACTGGAAGAACCGCACCCAGGAGCAGTGCGTGCACAACGAGACCAAGAACGAGCTGGAG
     |||||||||||| | |||||  || ||||| || ||||| |  |||||| |||  ||||
2221 TACTGGAAGAATCGGACCCAAGAACAGTGTGTTCACAATGAAACCAAGAATGAATTGGAG

2281 AAGATGCTGAAGTGCAACGAGGAGCACCCCGCCTACCTGGCCAGCGACGAGATCACCACC
     ||||||  ||| ||||  |||||||||| || || || || |||  |||| || |  | 
2281 AAGATGTTGAAATGTAATGAGGAGCACCCAGCTTATCTTGCAAGTGATGAAATAACCACA

2341 GTGCGCAAGAACCTGGAGAGCCGCGGCGTGGAGGTGGACCCCAGCCTGATCAAGGACACC
     || |  ||||||||  | | ||| | || || || || ||||| ||||| ||||| || 
2341 GTCCGGAAGAACCTTGAATCCCGAGGAGTAGAAGTAGATCCAAGCTTGATTAAGGATACT

2401 TGGCACCAGGTGTACCGCCGCCACTTCCTGAAGACCGCCCTGAACCACTGCAACCTGTGC
     ||||| |||||||| |  |  ||| | || |||||  | | ||| ||| |||||| | |
2401 TGGCATCAAGTTTATAGAAGACATTTTTTAAAAACAGCTCTAAACCATTGTAACCTTTGT

2461 CGCCGCGGCTTCTACTACTACCAGCGCCACTTCGTGGACAGCGAGCTGGAGTGCAACGAC
     ||  | ||  |  |||||||||| || ||| | || || |  || ||||| |||| || 
2461 CGAAGAGGTTTTTATTACTACCAAAGGCATTTTGTAGATTCTGAGTTGGAATGCAATGAT

2521 GTGGTGCTGTTCTGGCGCATCCAGCGCATGCTGGCCATCACCGCCAACACCCTGCGCCAG
     ||||| ||||| |||||  | |||||||||||| |||||| || || ||  | | |||| 
2521 GTGGTCTTGTTTTGGCGTATACAGCGCATGCTTGCTATCACCGCAAATACTTAAGGCAA

2581 CAGCTGACCAACACCGAGGTGCGCCGCCTGGAGAAGAACGTGAAGGAGGTGCTGGAGGAC
     ||| | || |||| |||  |  ||  | ||||  |||  ||||| || ||  |||| | 
2581 CAACTTACAAATACTGAAGTTAGGCGATTAGAGAAAAATGTTAAAGAGGTATTGGAAGAT

2641 TTCGCCGAGGACGGCGAGAAGAAGATCAAGCTGCTGACCGGCAAGCGCGTGCAGCTGGCC
     ||||| ||||| |  ||||||||||| || ||||||   |  |||||||||  |||| |
2641 TTTGCTGAAGATGGTGAGAAGAAGATTAAATTGCTTACTGGTAAACGCGTTCAACTGGCG

2701 GAGGACCTGAAGAAGGTGCGCGAGATCCAGGAGAAGCTGGACGCCTTCATCGAGGCCCTG
     || ||||| |||||  |   ||||  |||||||||||| | |  || ||||| || || 
2701 GAAGACCTCAAGAAAGTTAGAGAAATTCAAGAAAAACTTGATGCTTTCATTGAAGCTCTT

2761 CACCAGGAGAAGTAA
     || |||||| | |||
2761 CATCAGGAGAAATAA
```

(SEQ ID NO: 1 & 2)
Fig. 1 (continued)

Fig. 2

SEQUENCE LISTING

<160> NUMBER OF SEQ ID NOS: 19

<210> SEQ ID NO 1
<211> LENGTH: 2775
<212> TYPE: DNA
<213> ORGANISM: Artificial Sequence
<220> FEATURE:
<223> OTHER INFORMATION: Optimized hOPA1 gene sequence

<400> SEQUENCE: 1

```
atgtggcgcc tgcgccgcgc cgccgtggcc tgcgaggtgt gccagagcct ggtgaagcac      60
agcagcggca tcaagggcag cctgccctg cagaagctgc acctggtgag ccgcagcatc     120
taccacagcc accacccac cctgaagctg cagcgccccc agctgcgcac cagcttccag     180
cagttcagca gcctgaccaa cctgccctg cgcaagctga gttcagccc catcaagtac     240 ggctaccagc cccgccgcaa cttctggccc gcccgcctgg ccaccgcct gctgaagctg     300 cgctacctga tcctgggcag cgccgtgggc ggcggctaca ccgccaagaa gaccttcgac     360
cagtggaagg acatgatccc cgacctgagc gagtacaagt ggatcgtgcc cgacatcgtg     420
tgggagatcg acgagtacat cgacttcggc agccccgagg agaccgcctt ccgcgccacc     480
gaccgcggca gcgagagcga caagcacttc cgcaaggtga gcgacaagga gaagatcgac     540
cagctgcagg aggagctgct gcacacccag ctgaagtacc agcgcatcct ggagcgcctg     600
gagaaggaga acaaggagct gcgcaagctg gtgctgcaga aggacgacaa gggcatccac     660
caccgcaagc tgaagaagag cctgatcgac atgtacagcg aggtgctgga cgtgctgagc     720
gactacgacg ccagctacaa cacccaggac cacctgcccc gcgtggtggt ggtgggcgac     780
cagagcgccg gcaagaccag cgtgctggag atgatcgccc aggcccgcat cttcccccgc     840
ggcagcggcg agatgatgac ccgcagcccc gtgaaggtga ccctgagcga gggcccccac     900
cacgtggccc tgttcaagga cagcagccgc gagttcgacc tgaccaagga ggaggacctg     960
gccgccctgc gccacgagat cgagctgcgc atgcgcaaga acgtgaagga gggctgcacc    1020
gtgagccccg agaccatcag cctgaacgtg aagggccccg gcctgcagcg catggtgctg    1080
gtggacctgc ccggcgtgat caacaccgtg accagcggca tggccccga caccaaggag    1140 accatcttca gcatcagcaa ggcctacatg cagaaccca acgccatcat cctgtgcatc    1200
caggacggca gcgtggacgc cgagcgcagc atcgtgaccg acctggtgag ccagatggac    1260
ccccacggcc gccgcaccat cttcgtgctg accaaggtgg acctggccga agaacgtg    1320 gccagcccca gccgcatcca gcagatcatc gagggcaagc tgttcccat gaaggcctg    1380
```

```
ggctacttcg ccgtggtgac cggcaagggc aacagcagcg agagcatcga ggccatccgc   1440
gagtacgagg aggagttctt ccagaacagc aagctgctga agaccagcat gctgaaggcc   1500
caccaggtga ccacccgcaa cctgagcctg ccgtgagcg actgcttctg aagatggtg    1560 cgcgagagcg tggagcagca ggccgacagc ttcaaggcca cccgcttcaa cctggagacc   1620
gagtggaaga caactacccc cgcctgcgc gagctggacc gcaacgagct gttcgagaag    1680
gccaagaacg agatcctgga cgaggtgatc agcctgagcc aggtgacccc caagcactgg   1740
gaggagatcc tgcagcagag cctgtgggag cgcgtgagca cccacgtgat cgagaacatc   1800
tacctgcccg ccgcccagac catgaacagc ggcaccttca acaccaccgt ggacatcaag   1860
ctgaagcagt ggaccgacaa gcagctgccc aacaaggccg tggaggtggc ctgggagacc   1920
ctgcaggagg agttcagccg cttcatgacc gagcccaagg gcaaggagca cgacgacatc   1980
ttcgacaagc tgaaggaggc cgtgaaggag gagagcatca gccgccacaa gtggaacgac   2040
ttcgccgagg acagcctgcg cgtgatccag cacaacgccc tggaggaccg cagcatcagc   2100
gacaagcagc agtgggacgc cgccatctac ttcatggagg aggccctgca ggcccgcctg   2160
aaggacaccg agaacgccat cgagaacatg gtgggccccg actggaagaa cgctggctg    2220 tactggaaga accgcaccca ggagcagtgc gtgcacaacg agaccaagaa cgagctggag   2280
aagatgctga gtgcaacga ggagcacccc gcctacctgg ccagcgacga gatcaccacc    2340
gtgcgcaaga acctggagag ccgcggcgtg gaggtggacc ccagcctgat caaggacacc   2400
tggcaccagg tgtaccgccg ccacttcctg aagaccgccc tgaaccactg caacctgtgc   2460
cgccgcggct tctactacta ccagcgccac ttcgtggaca gcgagctgga gtgcaacgac   2520
gtggtgctgt tctggcgcat ccagcgcatg ctggccatca ccgccaacac cctgcgccag   2580
cagctgacca acaccgaggt cgccgcctg gagaagaacg tgaaggaggt gctggaggac    2640
ttcgccgagg acggcgagaa gaagatcaag ctgctgaccg caagcgcgt gcagctggcc    2700 gaggacctga agaaggtgcg cgagatccag gagaagctgg acgccttcat cgaggccctg   2760
caccaggaga agtaa                                                    2775
```

<210> SEQ ID NO 2
<211> LENGTH: 2775
<212> TYPE: DNA
<213> ORGANISM: Homo sapiens

<400> SEQUENCE: 2

```
atgtggcgac tacgtcgggc cgctgtggcc tgtgaggtct gccagtcttt agtgaaacac     60
agctctggaa taaaaggaag tttaccacta caaaaactac atctggtttc acgaagcatt    120
tatcattcac atcatcctac cttaaagctt caacgacccc aattaaggac atcctttcag    180
cagttctctt ctctgacaaa ccttccttta cgtaaactga aattctctcc aattaaatat    240
ggctaccagc ctcgcaggaa ttttggcca gcaagattag ctacgagact cttaaaactt     300
cgctatctca tactaggatc ggctgttggg ggtggctaca cagccaaaaa gacttttgat    360
cagtggaaag atatgatacc ggaccttagt gaatataaat ggattgtgcc tgacattgtg    420
tgggaaattg atgagtatat cgattttggt tctccggaag aaacggcgtt tagagcaaca    480
gatcgtggat ctgaaagtga caagcatttt agaaggtgt cagacaaaga gaaaattgac     540
caacttcagg aagaacttct gcacactcag ttgaagtatc agagaatctt ggaacgatta    600
gaaaaggaga acaaagaatt gagaaaatta gtattgcaga aagatgacaa aggcattcat    660
```

```
catagaaagc ttaagaaatc tttgattgac atgtattctg aagttcttga tgttctctct      720
gattatgatg ccagttataa tacgcaagat catctgccac gggttgttgt ggttggagat      780
cagagtgctg gaaagactag tgtgttggaa atgattgccc aagctcgaat attcccaaga      840
ggatctgggg agatgatgac acgttctcca gttaaggtga ctctgagtga aggtcctcac      900
catgtggccc tatttaaaga tagttctcgg gagtttgatc ttaccaaaga agaagatctt      960
gcagcattaa acatgaaat agaacttcga atgaggaaaa atgtgaaaga aggctgtacc      1020
gttagccctg agaccatatc cttaaatgta aaaggccctg gactacagag gatggtgctt      1080
gttgacttac caggtgtgat taatactgtg acatcaggca tggctcctga cacaaaggaa      1140
actatttcca gtatcagcaa agcttacatg cagaatccta atgccatcat actgtgtatt      1200
caagatggat ctgtggatgc tgaacgcagt attgttacag acttggtcag tcaaatggac      1260
cctcatggaa ggagaaccat attcgttttg accaaagtag acctggcaga gaaaaatgta      1320
gccagtccaa gcaggattca gcagataatt gaaggaaagc tcttcccaat gaaagcttta      1380
ggttattttg ctgttgtaac aggaaaaggg aacagctctg aaagcattga agctataaga      1440
gaatatgaag aagagttttt tcagaattca aagctcctaa agacaagcat gctaaaggca      1500
caccaagtga ctacaagaaa tttaagcctt gcagtatcag actgcttttg gaaatggta      1560
cgagagtctg ttgaacaaca ggctgatagt ttcaaagcaa cacgttttaa ccttgaaact      1620
gaatggaaga taactatcc tcgcctgcgg gaacttgacc ggaatgaact atttgaaaaa      1680
gctaaaaatg aaatccttga tgaagttatc agtctgagcc aggttacacc aaaacattgg      1740
gaggaaatcc ttcaacaatc tttgtgggaa agagtatcaa ctcatgtgat tgaaaacatc      1800
taccttccag ctgcgcagac catgaattca ggaactttta acaccacagt ggatatcaag      1860
cttaaacagt ggactgataa acaacttcct aataaagcag tagaggttgc ttgggagacc      1920
ctacaagaag aattttcccg ctttatgaca gaaccgaaag ggaaagagca tgatgacata      1980
tttgataaac ttaaagaggc tgttaaggaa gaaagtatta aacgacacaa gtggaatgac      2040
tttgcggagg acagcttgag ggttattcaa cacaatgctt ggaagaccg atccatatct      2100
gataaacagc aatgggatgc agctatttat tttatggaag aggctctgca ggctcgtctc      2160
aaggatactg aaaatgcaat tgaaacatg gtgggtccag actggaaaaa gaggtggtta      2220
tactggaaga atcggaccca agaacagtgt gttcacaatg aaaccaagaa tgaattggag      2280
aagatgttga atgtaatga ggagcaccca gcttatcttg caagtgatga ataaccaca      2340
gtccggaaga accttgaatc ccgaggagta gaagtagatc caagcttgat taaggatact      2400
tggcatcaag tttatagaag acatttttta aaaacagctc taaaccattg taacctttgt      2460
cgaagaggtt tttattacta ccaaaggcat tttgtagatt ctgagttgga atgcaatgat      2520
gtggtcttgt tttggcgtat acagcgcatg cttgctatca ccgcaaatac tttaaggcaa      2580
caacttacaa atactgaagt taggcgatta gagaaaaatg ttaaagaggt attggaagat      2640
tttgctgaag atggtgagaa gaagattaaa ttgcttactg gtaaacgcgt tcaactggcg      2700
gaagacctca gaaagttag agaaattcaa gaaaaacttg atgctttcat tgaagctctt      2760
catcaggaga aataa                                                       2775
```

<210> SEQ ID NO 3
<211> LENGTH: 924
<212> TYPE: PRT
<213> ORGANISM: Homo sapiens

<400> SEQUENCE: 3

```
Met Trp Arg Leu Arg Arg Ala Ala Val Ala Cys Glu Val Cys Gln Ser
1               5                   10                  15

Leu Val Lys His Ser Ser Gly Ile Lys Gly Ser Leu Pro Leu Gln Lys
            20                  25                  30

Leu His Leu Val Ser Arg Ser Ile Tyr His Ser His His Pro Thr Leu
        35                  40                  45

Lys Leu Gln Arg Pro Gln Leu Arg Thr Ser Phe Gln Gln Phe Ser Ser
    50                  55                  60

Leu Thr Asn Leu Pro Leu Arg Lys Leu Lys Phe Ser Pro Ile Lys Tyr
65                  70                  75                  80

Gly Tyr Gln Pro Arg Arg Asn Phe Trp Pro Ala Arg Leu Ala Thr Arg
                85                  90                  95

Leu Leu Lys Leu Arg Tyr Leu Ile Leu Gly Ser Ala Val Gly Gly Gly
            100                 105                 110

Tyr Thr Ala Lys Lys Thr Phe Asp Gln Trp Lys Asp Met Ile Pro Asp
        115                 120                 125

Leu Ser Glu Tyr Lys Trp Ile Val Pro Asp Ile Val Trp Glu Ile Asp
    130                 135                 140

Glu Tyr Ile Asp Phe Gly Ser Pro Glu Thr Ala Phe Arg Ala Thr
145                 150                 155                 160

Asp Arg Gly Ser Glu Ser Asp Lys His Phe Arg Lys Val Ser Asp Lys
                165                 170                 175

Glu Lys Ile Asp Gln Leu Gln Glu Glu Leu Leu His Thr Gln Leu Lys
            180                 185                 190

Tyr Gln Arg Ile Leu Glu Arg Leu Glu Lys Glu Asn Lys Glu Leu Arg
        195                 200                 205

Lys Leu Val Leu Gln Lys Asp Asp Lys Gly Ile His His Arg Lys Leu
    210                 215                 220

Lys Lys Ser Leu Ile Asp Met Tyr Ser Glu Val Leu Asp Val Leu Ser
225                 230                 235                 240

Asp Tyr Asp Ala Ser Tyr Asn Thr Gln Asp His Leu Pro Arg Val Val
                245                 250                 255

Val Val Gly Asp Gln Ser Ala Gly Lys Thr Ser Val Leu Glu Met Ile
            260                 265                 270

Ala Gln Ala Arg Ile Phe Pro Arg Gly Ser Gly Glu Met Met Thr Arg
        275                 280                 285

Ser Pro Val Lys Val Thr Leu Ser Glu Gly Pro His His Val Ala Leu
    290                 295                 300

Phe Lys Asp Ser Ser Arg Glu Phe Asp Leu Thr Lys Glu Glu Asp Leu
305                 310                 315                 320

Ala Ala Leu Arg His Glu Ile Glu Leu Arg Met Arg Lys Asn Val Lys
                325                 330                 335

Glu Gly Cys Thr Val Ser Pro Glu Thr Ile Ser Leu Asn Val Lys Gly
            340                 345                 350

Pro Gly Leu Gln Arg Met Val Leu Val Asp Leu Pro Gly Val Ile Asn
        355                 360                 365

Thr Val Thr Ser Gly Met Ala Pro Asp Thr Lys Glu Thr Ile Phe Ser
    370                 375                 380

Ile Ser Lys Ala Tyr Met Gln Asn Pro Asn Ala Ile Ile Leu Cys Ile
385                 390                 395                 400

Gln Asp Gly Ser Val Asp Ala Glu Arg Ser Ile Val Thr Asp Leu Val
                405                 410                 415
```

-continued

```
Ser Gln Met Asp Pro His Gly Arg Arg Thr Ile Phe Val Leu Thr Lys
            420                 425                 430
Val Asp Leu Ala Glu Lys Asn Val Ala Ser Pro Ser Arg Ile Gln Gln
        435                 440                 445
Ile Ile Glu Gly Lys Leu Phe Pro Met Lys Ala Leu Gly Tyr Phe Ala
    450                 455                 460
Val Val Thr Gly Lys Gly Asn Ser Ser Glu Ser Ile Glu Ala Ile Arg
465                 470                 475                 480
Glu Tyr Glu Glu Glu Phe Phe Gln Asn Ser Lys Leu Leu Lys Thr Ser
                485                 490                 495
Met Leu Lys Ala His Gln Val Thr Thr Arg Asn Leu Ser Leu Ala Val
            500                 505                 510
Ser Asp Cys Phe Trp Lys Met Val Arg Glu Ser Val Glu Gln Gln Ala
        515                 520                 525
Asp Ser Phe Lys Ala Thr Arg Phe Asn Leu Glu Thr Glu Trp Lys Asn
    530                 535                 540
Asn Tyr Pro Arg Leu Arg Glu Leu Asp Arg Asn Glu Leu Phe Glu Lys
545                 550                 555                 560
Ala Lys Asn Glu Ile Leu Asp Glu Val Ile Ser Leu Ser Gln Val Thr
                565                 570                 575
Pro Lys His Trp Glu Glu Ile Leu Gln Gln Ser Leu Trp Glu Arg Val
            580                 585                 590
Ser Thr His Val Ile Glu Asn Ile Tyr Leu Pro Ala Ala Gln Thr Met
        595                 600                 605
Asn Ser Gly Thr Phe Asn Thr Thr Val Asp Ile Lys Leu Lys Gln Trp
    610                 615                 620
Thr Asp Lys Gln Leu Pro Asn Lys Ala Val Glu Val Ala Trp Glu Thr
625                 630                 635                 640
Leu Gln Glu Glu Phe Ser Arg Phe Met Thr Glu Pro Lys Gly Lys Glu
                645                 650                 655
His Asp Asp Ile Phe Asp Lys Leu Lys Glu Ala Val Lys Glu Glu Ser
            660                 665                 670
Ile Lys Arg His Lys Trp Asn Asp Phe Ala Glu Asp Ser Leu Arg Val
        675                 680                 685
Ile Gln His Asn Ala Leu Glu Asp Arg Ser Ile Ser Asp Lys Gln Gln
    690                 695                 700
Trp Asp Ala Ala Ile Tyr Phe Met Glu Glu Ala Leu Gln Ala Arg Leu
705                 710                 715                 720
Lys Asp Thr Glu Asn Ala Ile Glu Asn Met Val Gly Pro Asp Trp Lys
                725                 730                 735
Lys Arg Trp Leu Tyr Trp Lys Asn Arg Thr Gln Glu Gln Cys Val His
            740                 745                 750
Asn Glu Thr Lys Asn Glu Leu Glu Lys Met Leu Lys Cys Asn Glu Glu
        755                 760                 765
His Pro Ala Tyr Leu Ala Ser Asp Glu Ile Thr Thr Val Arg Lys Asn
    770                 775                 780
Leu Glu Ser Arg Gly Val Glu Val Asp Pro Ser Leu Ile Lys Asp Thr
785                 790                 795                 800
Trp His Gln Val Tyr Arg Arg His Phe Leu Lys Thr Ala Leu Asn His
                805                 810                 815
Cys Asn Leu Cys Arg Arg Gly Phe Tyr Tyr Gln Arg His Phe Val
            820                 825                 830
Asp Ser Glu Leu Glu Cys Asn Asp Val Val Leu Phe Trp Arg Ile Gln
```

```
                835                 840                 845
Arg Met Leu Ala Ile Thr Ala Asn Thr Leu Arg Gln Gln Leu Thr Asn
        850                 855                 860

Thr Glu Val Arg Arg Leu Glu Lys Asn Val Lys Val Leu Glu Asp
865                 870                 875                 880

Phe Ala Glu Asp Gly Glu Lys Lys Ile Lys Leu Leu Thr Gly Lys Arg
                    885                 890                 895

Val Gln Leu Ala Glu Asp Leu Lys Lys Val Arg Glu Ile Gln Glu Lys
        900                 905                 910

Leu Asp Ala Phe Ile Glu Ala Leu His Gln Glu Lys
            915                 920

<210> SEQ ID NO 4
<211> LENGTH: 17
<212> TYPE: DNA
<213> ORGANISM: Artificial Sequence
<220> FEATURE:
<223> OTHER INFORMATION: Primer

<400> SEQUENCE: 4
atgtggcgac tacgtcg                                                17

<210> SEQ ID NO 5
<211> LENGTH: 20
<212> TYPE: DNA
<213> ORGANISM: Artificial Sequence
<220> FEATURE:
<223> OTHER INFORMATION: Primer

<400> SEQUENCE: 5
ttatttctcc tgatgaagag                                             20

<210> SEQ ID NO 6
<211> LENGTH: 20
<212> TYPE: DNA
<213> ORGANISM: Oryctolagus cuniculus

<400> SEQUENCE: 6
ccttctacaa cgagctgcgc                                             20

<210> SEQ ID NO 7
<211> LENGTH: 18
<212> TYPE: DNA
<213> ORGANISM: Oryctolagus cuniculus

<400> SEQUENCE: 7
tacagggaca gcacggcc                                               18

<210> SEQ ID NO 8
<211> LENGTH: 20
<212> TYPE: DNA
<213> ORGANISM: Homo sapiens

<400> SEQUENCE: 8
ttaggttatt ttgctgttgt                                             20

<210> SEQ ID NO 9
<211> LENGTH: 20
<212> TYPE: DNA
<213> ORGANISM: Homo sapiens

<400> SEQUENCE: 9
```

```
ttgtagtcac ttggtgtgcc                                                     20

<210> SEQ ID NO 10
<211> LENGTH: 20
<212> TYPE: DNA
<213> ORGANISM: Artificial Sequence
<220> FEATURE:
<223> OTHER INFORMATION: Primer

<400> SEQUENCE: 10
ctgggctact tcgccgtggt                                                     20

<210> SEQ ID NO 11
<211> LENGTH: 20
<212> TYPE: DNA
<213> ORGANISM: Artificial Sequence
<220> FEATURE:
<223> OTHER INFORMATION: Primer

<400> SEQUENCE: 11
gggtggtcac ctggtgggcc                                                     20

<210> SEQ ID NO 12
<211> LENGTH: 22
<212> TYPE: DNA
<213> ORGANISM: Artificial Sequence
<220> FEATURE:
<223> OTHER INFORMATION: Primer

<400> SEQUENCE: 12
ctttaggtta ttttgctgtt gt                                                  22

<210> SEQ ID NO 13
<211> LENGTH: 20
<212> TYPE: DNA
<213> ORGANISM: Artificial Sequence
<220> FEATURE:
<223> OTHER INFORMATION: Primer

<400> SEQUENCE: 13
ttgtagtcac ttggtgtgcc                                                     20

<210> SEQ ID NO 14
<211> LENGTH: 1150
<212> TYPE: DNA
<213> ORGANISM: Mus musculus

<400> SEQUENCE: 14
ttgcactgca gccttcccag ttcttaggct gcgtaagctc tcttgcttga acactgaccc         60
tgaccacttc tctactctgt tccaggctct cacacgcccg tgctcccagc ctgtctcttac       120 acgcatgcgc tccctgccta atactccttc cccttcttct ctgttctcac agagcctagt       180
cttggcagag tgtgatttct ctgttagttg gtcacctgac agtgtatttg actcttatgg       240
tgttaatggt taactcatta atgttaatag ctttctctt ttactgtcta actagattat        300
gaaatcctaa attaataaat aaactgaaga agtagcatta attcttatac tagttttact       360
atgaaaacat atagtaagaa aaaacaatg caaatttgaa tgtatctaca ttttctcttc        420
atgtatctgt ggtctttgtt ttattttcac tgacttttgc taattttaat tttttgcag        480 aaatctttga ttgatatgta ttctgaagtt cttgatgttc tttctgatta tgatgccagt       540
tacaatacac aagatcacct accacgggta aggggaaaat agaccaggac ctgctgtcag       600
caggaaagtt ctttccttgt gtcatagtaa tttctgtatt tcccatgata cctcagatac       660
```

-continued

```
aaagcattgc ttcgttcctt attttggaga ccataaaagc aaatatatat gttttggaag    720
aaaaatgtca gatatttgcc attatacatt cattatagtg ttaaaatacc taggcaaaaa    780
ctgtaaacgt ttggatgaaa tttagtctaa cagaatccaa aagtatgttt gtaaatgta     840 aactggttat ggaaaatatt tgtggaaagt taatgatctg ttttagaaaa taactttcaa    900
ttggcatagt tttcaaaaca aaatttgaa tgtaaatagt ggagccaatt aattcttttg     960
ctatatgtat ctccagagta cctacatgca tcaaacttca ttctttcaaa aaaaaaagaa    1020
aacaaacaaa caaacacttt ttttggctct aaatatctta aaatatgttt taaatgataa    1080
cattcaaacc ctacatacat ttaatttggt atcagaagag aactaatgta tgctccttgt    1140
cttgtgatag                                                          1150
```

<210> SEQ ID NO 15
<211> LENGTH: 23
<212> TYPE: DNA
<213> ORGANISM: Artificial Sequence
<220> FEATURE:
<223> OTHER INFORMATION: DNA sequence corresponding to sgRNA1

<400> SEQUENCE: 15
atacacaaga tcacctacca cgg    23

<210> SEQ ID NO 16
<211> LENGTH: 23
<212> TYPE: DNA
<213> ORGANISM: Artificial Sequence
<220> FEATURE:
<223> OTHER INFORMATION: DNA sequence corresponding to sgRNA2

<400> SEQUENCE: 16
ccagttacaa tacacaagat cac    23

<210> SEQ ID NO 17
<211> LENGTH: 120
<212> TYPE: DNA
<213> ORGANISM: Artificial Sequence
<220> FEATURE:
<223> OTHER INFORMATION: Homologous fragment for introducing point
      mutation

<400> SEQUENCE: 17
ttgatatgta ttctgaagtt cttgatgttc tttctgatta tgatgccagt tacaatacat    60
aagatcacct accacgggta aggggaaaat agaccaggac ctgctgtcag caggaaagtt    120

<210> SEQ ID NO 18
<211> LENGTH: 54
<212> TYPE: DNA
<213> ORGANISM: Artificial Sequence
<220> FEATURE:
<223> OTHER INFORMATION: point mutation of ADOA

<400> SEQUENCE: 18
attatgatgc cagttacaat acataagatc acctaccacg ggtaagggga aaat    54

<210> SEQ ID NO 19
<211> LENGTH: 54
<212> TYPE: DNA
<213> ORGANISM: Mus musculus

```
<400> SEQUENCE: 19
attatgatgc cagttacaat acacaagatc acctaccacg ggtaaggggga aaat        54
```

GENE SEQUENCE OF RECOMBINANT HUMAN TYPE II MITOCHONDRIAL DYNEIN-LIKE GTPASE AND USES THEREOF

CROSS-REFERENCE TO RELATED APPLICATIONS

This application is a continuation application of PCT Application No. PCT/CN2019/102352, filed on Aug. 23, 2019, which claims the benefit of Chinese Application No. CN201810968173.0, filed on Aug. 23, 2018; each of which is incorporated herein by reference in its entirety.

REFERENCE TO A SEQUENCE LISTING

The instant application contains a Sequence Listing which has been submitted in ASCII format via EFS-Web and is hereby incorporated by reference in its entirety. Said ASCII copy, created on Jul. 28, 2021, is named WNBT_012_01US SubSeqList_ST25.txt and is about 19.7 kb in size.

FIELD

The invention relates to the field of biological preparations, in particular to the gene sequence of recombinant human type II mitochondrial dynein-like GTPase and uses thereof.

BACKGROUND

Autosomal dominant optic atrophy (ADOA) is the most common form of primary hereditary optic neuropathy, with an incidence ratio of about 1:12,000 to 1:50,000, and it's onset is insidious in childhood. Its clinical characteristics are manifested by mild to moderate gradual loss of vision, color vision deficiencies, central visual field defects, and temporal optic disc pallor. Firstly, the papillary vascular bundles are injured, followed by the ascending atrophy of optic nerves and the loss of the myelin sheaths of optic nerves.

ADOA is caused by mutations in genes encoding internal mitochondrial membrane proteins and loci, and foreign scholars have determined that these genes are mainly OPA1-OPA8; among them, it has been initially confirmed that about 75% of ADOA patients are related to heterozygous and dominant mutations carried by OPA1, in which the site mutations in nucleotides 740 and 2794 are most common. OPA1 proteins locate at the inner mitochondrial membranes, control the energy metabolism and apoptosis, maintain the integrity of cristae and mtDNA, and have GTPase activities. The pathogenesis of ADOA lies in that mutant OPA1 encodes a variety of truncated forms of proteins usually lacking complete GTPase domains, that is equivalent to the deletion of an allele, which will greatly reduce the amount of OPA1, resulting in a so-called haplotype insufficiency, thus the mitochondrial functions are impaired. Fragmented mitochondria cannot supply ATP normally for optic nerve cells, and RGC cells gradually undergo apoptosis, which leads to the occurrence of ADOA in patients.

Currently, there is no treatment means for ADOA, and it is one of the world's recognized hereditary optic neuropathies. With the development of gene therapy, the gene therapy of ADOA has become possible, and the difficulties therein are the various forms of OPA1 exon splicing and various forms of mutations, which cause a variety of types and mutation forms of pathogenic proteins, resulting that it is impossible to use a certain gene drug to treat all patients.

In foreign studies, people have studied the pathogenesis of ADOA caused by OPA1 mutations, analyzed the various forms of OPA1 transcription and gene products, and explored the better purification methods for recombinant OPA1 proteins. In addition, family medical histories have been investigated and analyzed to seek how to screen, identify and diagnose whether a defective OPA1 is carried. Furthermore, the prognostic genetic diagnosis and treatment of ADOA caused by OPA1 mutations also have been expected. However, there are currently no reports of recombination of genes of any type of human mitochondrial dynein-like GTPases using adeno-associated virus vectors, as well as the production and uses thereof.

Therefore, there is an urgent need in this field to develop an expression system and preparation method for a human mitochondrial dynein-like GTPase having good therapeutic effects.

SUMMARY

The purpose of the present invention is to provide an expression system for a human mitochondrial dynein-like GTPase having good therapeutic effects and a preparation method thereof.

The purpose of the present invention is to provide an optimized nucleic acid sequence for encoding a human mitochondrial dynein-like GTPase, a vector and a preparation method thereof.

The first aspect of the present invention provides a nucleotide sequence encoding a human type II mitochondrial dynein-like GTPase, and the nucleotide sequence is selected from the group consisting of:

(a) a nucleotide sequence shown in SEQ ID NO: 1; and (b) a nucleotide sequence being ≥95%, preferably ≥98%, and more preferably ≥99% identical to the nucleotide sequence shown in SEQ ID NO: 1.

In another preferred embodiment, the nucleotide sequence includes a DNA sequence, a cDNA sequence or an mRNA sequence.

In another preferred embodiment, the nucleotide sequence includes a single-stranded sequence and a double-stranded sequence.

In another preferred embodiment, the nucleotide sequence includes a nucleotide sequence that is completely complementary to SEQ ID NO: 1.

In another preferred embodiment, the nucleotide sequence is shown in SEQ ID NO: 1, wherein positions 1-288 are the coding sequence of MIS;

positions 289-2772 are the coding sequences of a GTPase domain, a central dynein domain and a GTPase effector domain;

and positions 2773-2775 are a stop codon.

In another preferred embodiment, the sequence of SEQ ID NO: 1 comprises: MIS coding sequence as shown in positions 1-288 in SEQ ID NO: 1; and the coding sequence of the GTPase domain, the central dynein domain and the GTPase effector domain as shown in positions 289-2772 in SEQ ID NO: 1.

In another preferred embodiment, the sequence of SEQ ID NO: 2 comprises: MIS coding sequence as shown in positions 1-288 in SEQ ID NO: 2; and the coding sequence of the GTPase domain, the central dynein domain and the GTPase effector domain as shown in positions 289-2772 in SEQ ID NO: 2. The present invention also provides the nucleotide sequence (positions 1-288 in SEQ ID NO: 1 or 2) separately encoding the MIS, and the nucleotide sequences (positions 289-2772 or 289-2775 in SEQ ID NO: 1 or 2)

separately encoding the GTPase domain, the central dynein domain and the GTPase effector domain.

The second aspect of the present invention provides a fusion nucleic acid comprising the nucleotide sequence as described in the first aspect of the present invention.

In another preferred embodiment, the fusion nucleic acid further comprises a sequence selected from the group consisting of a UTR sequence, a promoter sequence or a combination thereof.

In another preferred embodiment, the UTR sequence includes a 3'-UTR and/or a 5'-UTR.

In another preferred embodiment, the UTR sequence contains a polyA sequence for stabilizing the structure.

In another preferred embodiment, the fusion nucleic acid has a structure of formula I from the 5'-end to the 3'-end:

Z1-Z2-Z3    (I)

wherein each "-" is independently a bond or a nucleotide linker sequence;

Z1 is null or a 5'-UTR sequence;

Z2 is the nucleotide sequence as described in the first aspect of the present invention; and Z3 is a 3'-UTR sequence.

In another preferred embodiment, the Z1 is a 5'-UTR sequence.

In another preferred embodiment, the length of each nucleotide linker sequence is 1-30 nt, preferably 1-15 nt, and more preferably 3-6 nt.

In another preferred embodiment, the nucleotide linker sequence is derived from a nucleotide linker sequence formed by digestion via a restriction endonuclease.

The third aspect of the present invention provides a vector containing the nucleotide sequence according to the first aspect of the present invention or the fusion nucleic acid according to the second aspect of the present invention.

In another preferred embodiment, the vector comprises one or more promoters, which are operably linked to the nucleic acid sequence, an enhancer, a transcription termination signal, a polyadenylation sequence, an origin of replication, a selectable marker, a nucleic acid restriction site and/or a homologous recombination site.

In another preferred embodiment, the vector is selected from the group consisting of a plasmid and a viral vector.

In another preferred embodiment, the vector is selected from the group consisting of a lentivirus vector, an adenovirus vector, an adeno-associated virus vector or a combination thereof. Preferably, the vector is an AAV vector.

In another preferred embodiment, the serotypes of the AAV vector is selected from AAV2, AAV5, AAV7, AAV8 or a combination thereof.

In another preferred embodiment, the vector includes a DNA virus and a retroviral vector.

In another preferred embodiment, the vector is an AAV vector containing or inserted with the nucleotide sequence described in the first aspect of the present invention or the fusion nucleic acid described in the second aspect of the present invention; preferably, the vector is an AAV vector plasmid pSNaV.

In another preferred embodiment, the vector is used for expressing the recombinant human type II mitochondrial dynein-like GTPase.

The fourth aspect of the present invention provides a host cell, said host cell contains the vector described in the third aspect of the present invention, or the host cell has the nucleotide sequence described in the first aspect of the present invention or the fusion nucleic acid described in the second aspect of the present invention that is exogenously integrated into its chromosome.

In another preferred embodiment, the host cell is a mammalian cell, and the mammal includes a human and a non-human mammal.

In another preferred embodiment, the host cell is selected from the group consisting of a 293T cell, a photoreceptor cell (including a cone cell and/or a rod cell), other visual cells (such as a bipolar cell), an (optic) nerve cell or a combination thereof.

In another preferred embodiment, the host cell is selected from the group consisting of a rod cell, a cone cell, an on-bipolar cell, an off-bipolar cell, a horizontal cell, a ganglion cell, an amacrine cell or a combination thereof. Preferably, the host cell is a (retinal) ganglion cell.

The fifth aspect of the present invention provides the use of the vector described in the third aspect of the present invention in preparing a preparation or a composition for restoring the vision and/or treating the eye diseases in a subject.

In another preferred embodiment, the eye disease is retinopathy.

In another preferred embodiment, the preparation or the composition is used for treating hereditary optic neuropathy, preferably autosomal dominant optic atrophy (ADOA).

In another preferred embodiment, the preparation or the composition is used for treating retinal ganglion cell apoptosis.

The sixth aspect of the present invention provides a pharmaceutical preparation which contains (a) the vector described in the third aspect of the present invention, and (b) a pharmaceutically acceptable carrier or excipient.

In another preferred embodiment, the dosage form of the pharmaceutical preparation is selected from the group consisting of a lyophilized preparation, a liquid preparation or a combination thereof.

In another preferred embodiment, the vector is selected from the group consisting of a lentivirus vector, an adenovirus vector, an adeno-associated virus vector or a combination thereof. Preferably, the vector is an AAV vector.

In another preferred embodiment, the content of the vector in the pharmaceutical preparation is $1 \times 10^9$-$1 \times 10^{16}$, preferably $1 \times 10^1$-$1 \times 10^{13}$ viruses/mL, and more preferably $2 \times 10^{11}$-$1 \times 10^{12}$ viruses/mL.

In another preferred embodiment, the pharmaceutical preparation is used for treating eye diseases, preferably for treating retinal ganglion cell apoptosis.

In another preferred embodiment, the pharmaceutical preparation is used for treating hereditary optic neuropathy, preferably autosomal dominant optic atrophy (ADOA).

In another preferred embodiment, the pharmaceutical preparation can significantly increase the expression and/or activity of mitochondrial dynein-like GTPase in eyeball.

The seventh aspect of the present invention provides a method for increasing the expression and/or activity of a mitochondrial dynein-like GTPase for a long time, in which the method comprises introducing the vector described in the third aspect of the present invention, and/or administering the pharmaceutical preparation described in the sixth aspect of the present invention.

In another preferred embodiment, the method can effectively increase the content of ATP produced in a cell and/or inhibit mitochondrial apoptosis.

In another preferred embodiment, the method can continuously up-regulate the expression and/or activity of GTPases.

The eighth aspect of the present invention provides a treatment method, which comprises administering the vector described in the third aspect of the present invention to a subject in need thereof.

In another preferred embodiment, the vector is selected from the group consisting of a lentivirus vector, an adenovirus vector, an adeno-associated virus vector or a combination thereof. Preferably, the vector is an AAV vector.

In another preferred embodiment, the vector is introduced into the eye of a subject in need thereof.

In another preferred embodiment, the subject in need thereof includes a human and a non-human mammal.

In another preferred embodiment, the treatment method is a method for treating eye diseases.

In another preferred embodiment, the eye disease is hereditary optic neuropathy, preferably autosomal dominant optic atrophy (ADOA).

The treatment method can effectively increase the expression and/or activity of mitochondrial dynein-like GTPase in eyeball.

The treatment method can effectively increase the expression and/or activity of mitochondrial dynein-like GTPase in eyeball for up to 6 months, preferably up to 3 months.

The treatment method can effectively increase retinal ATP content and/or inhibit mitochondrial apoptosis.

The ninth aspect of the present invention provides a method for preparing a recombinant human type II mitochondrial dynein-like GTPase, which comprises culturing the host cell described in the fourth aspect of the present invention, thereby obtaining the recombinant human type II mitochondrial dynein-like GTPase.

The tenth aspect of the present invention provides a cell model of ADOA (autosomal dominant optic atrophy) in which the expression or viability of OPA1 gene is decreased.

In another preferred embodiment, the cell includes a retinal ganglion cell (RGC).

In another preferred embodiment, the OPA1 gene is not expressed or inactive completely.

The eleventh aspect of the present invention provides a method for preparing a cell model of ADOA (autosomal dominant optic atrophy), which comprises providing a cell and performing a point mutation on the OPA1 gene in the cells to obtain the cells having the point mutation of the OPA1 gene; and obtaining the monoclonal cells that have a positive point mutation through screening.

In another preferred embodiment, the OPA1 gene point mutation refers to a Q(glutamine) 285 Stop point mutation.

In another preferred embodiment, the cell include a RGC cell.

The twelfth aspect of the present invention provides a non-human mammalian model of ADOA (autosomal dominant optic atrophy) in which the expression and/or viability of OPA1 gene in GRC cells are reduced.

In another preferred embodiment, the OPA1 gene has a point mutation, specifically, a Q (glutamine) 285 Stop point mutation.

The thirteenth aspect of the present invention provides a method for preparing a non-human mammalian model of ADOA (autosomal dominant optic atrophy), which comprises the following steps:

(a) providing a non-human mammalian cell, performing a point mutation on the OPA1 gene in the cells, thereby obtaining the cells having the point mutation of the OPA1 gene;

(b preparing an animal model having the point mutation of the OPA1 gene by using the cells having the point mutation of the OPA1 gene obtained in step (a).

In another preferred embodiment, the point mutation of the OPA1 gene is heterozygous or homozygous.

In another preferred embodiment, the glutamine site at position 285 of the OPA1 protein is mutated for transcription termination.

In another preferred embodiment, the non-human mammal is a rodent or a primate, preferably including a mouse, a rat, a rabbit, and a monkey.

In another preferred embodiment, step (b) includes the step of:

(b1) preparing an animal model which has obtained a chimeric point mutation of the OPA1 gene, and then obtaining an animal model having homozygous or heterozygous point mutation of the OPA1 gene through crossing;

In another preferred embodiment, the method comprises:

(1) constructing a recombinant plasmid having a mutation of Q (glutamine) at position 285 of OPA1 into a stop (i.e., Q285 Stop) point mutation by using CRISPR-CAS9 technology, and replacing with a DNA sequence having a selectable marker for homologous mutation to obtain a monoclonal embryonic stem cell having a positive point mutation Q285 Stop of OPA1;

(2) preparing and obtaining chimeric mice by using the mouse embryonic stem cell clone having OPA1 point mutation obtained in step (1);

(3) allowing the chimeric mice obtained in step (2) to mate with normal wild-type mice and breed, and screening heterozygous mice from the offspring that obtained OPA1 point mutation, i.e., the mouse model having Q285 Stop point mutation of OPA1.

In another preferred embodiment, the heterozygous mice are allowed to undergo mating and breeding, and homozygous mice that obtained OPA1 point mutation are screened from their offspring.

It should be understood that all of the various technical features described above and the various technical features specifically described hereinafter (such as examples) can be combined with one another within the scope of the present invention, so as to form new or preferred technical solutions. Due to space limitations, they will not be repeated here.

BRIEF DESCRIPTION OF THE DRAWINGS

FIG. 1 shows the comparison of open reading frame sequences between the optimized nucleotide sequence and the original gene sequence of human type II mitochondrial dynein-like GTPase. The homology between the two sequences is 72.25% (2005/2775), among which the identical bases are indicated by "|", the upper row is the optimized open reading frame nucleotide sequence, and the lower row is the original gene sequence of human type II mitochondrial dynein-like GTPase (unoptimized wild coding sequence).

FIG. 2 shows the schematic diagram of the protein structure of the transcript of OPA1 isoform 2.

DETAILED DESCRIPTION

Figure 3:
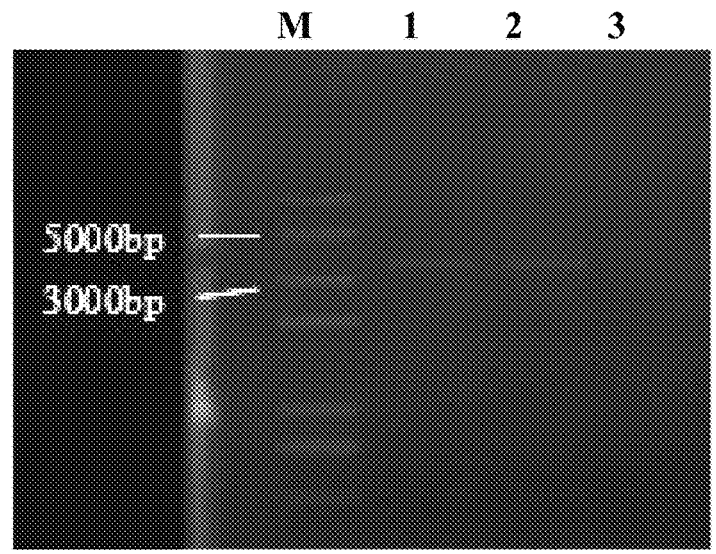
FIG. 3 shows the correct clone with a target band of about 3000 bp screened from the recombinant clones, M: protein marker; lane 1: correct recombinant clone of rAAV2/2-hOPA1 isoform 2; lane 2: positive control; lane 3: negative control.

After extensive and in-depth research, the inventors have carried out targeted optimization design on the gene coding sequence of recombinant human type II mitochondrial dynein-like GTPase (OPA1), so as to obtain a nucleotide sequence (SEQ ID NO: 1) which is particularly suited to be efficiently transcribed and efficiently express OPA1 protein in mammalian (such as human) cells, and construct a recombinant expression vector for the recombinant human type II mitochondrial dynein-like GTPase. The experimental results show that, as compared with the unoptimized coding sequence, the specially optimized OPA1 coding sequence (SEQ ID NO: 1) has slightly improved transcription efficiency, and the expression amount thereof has been significantly increased by more than 5 times, which is very suited to be expressed in a mammalian (especially a human) cells, and it can effectively treat ADOA and other eye diseases. The present invention is accomplished by the inventors on this basis.

Definitions

Certain terms are firstly defined in order to make this disclosure be more easily understood. As used in this application, each of the following terms shall have the meanings given as follows unless expressly stated otherwise herein. Other definitions are stated throughout the application.

The term "about" may refer to a value or composition within an acceptable error range of a particular value or composition determined by a person of ordinary skill in the art, which will partially depend on how the value or composition is measured or determined. For example, as used herein, the expression "about 100" includes all values between 99 and 101 (for example, 99.1, 99.2, 99.3, 99.4, etc.).

As used herein, the terms "comprising" or "including (containing)" can be open, semi-closed and closed. In other words, the terms also include "essentially consisting of" or "consisting of".

Sequence identity is determined by comparing two aligned sequences along a predetermined comparison window (which can be 50%, 60%, 70%, 80%, 90%, 95% or 100% of the length of the reference nucleotide sequence or protein) and determining the number of positions where the identical residues appear. Usually, this is expressed as a percentage. The measurement of sequence identity of nucleotide sequences is a method well known to those skilled in the art.

As used herein, the terms "subject" and "subject in need thereof" refer to any mammals or non-mammals. Mammals include but are not limited to human beings, vertebrates such as rodents, non-human primates, cattle, horses, dogs, cats, pigs, sheep and goats.

OPA1 (optic atrophy 1)

As used herein, the terms "(recombinant) human type II mitochondrial dynein-like GTPase", "optic atrophy protein 1", "OPA1 (protein)", "hOPA1 (protein)", "polypeptide", "polypeptide of the present invention" and "protein of the present invention" have the same meanings and can be used interchangeably herein. OPA1 is a transmembrane protein with GTPase activity located in the inner mitochondrial membrane; and this protein comprises an N-terminal transmembrane region having a mitochondrial import sequence (MIS), a transmembrane region (TR) and a hydrophobic region (HR), a GTPase domain, a central dynein domain, and a C-terminal having a GTPase effector domain (GED). The function of MIS polypeptide of OPA1 is to guide GTP protein into mitochondria.

ADOA is caused by mutations in genes encoding internal mitochondrial membrane proteins and loci, and foreign scholars have determined that these genes are mainly OPA1-OPA8; among them, it has been initially confirmed that about 75% of ADOA patients are related to heterozygous and dominant mutations carried by OPA1, in which the site mutations in nucleotides 740 and 2794 are most common. OPA1 proteins locate at the inner mitochondrial membranes, control the energy metabolism and apoptosis, maintain the integrity of cristae and mtDNA, and have GTPase activities. The pathogenesis of ADOA lies in that mutant OPA1 encodes a variety of truncated forms of proteins usually lacking complete GTPase domains, that is equivalent to the deletion of an allele, which will greatly reduce the amount of OPA1, resulting in a so-called haplotype insufficiency, thus the mitochondrial functions are impaired. Fragmented mitochondria cannot supply ATP normally for optic nerve cells, and RGC cells gradually undergo apoptosis, which leads to the occurrence of ADOA in patients.

Adeno-Associated Virus

Adeno-associated virus (AAV), also known as Adeno-Associated Virus, belongs to the Dependovirus in Parvoviridae. It is the simplest type of single-stranded DNA-defective virus found so far and requires a helper virus (usually adenovirus) to participate in its replication. It encodes the cap and rep genes in the inverted repeats (ITR) at both ends. ITRs play a decisive role in virus replication and packaging. The cap gene encodes the viral capsid protein and the rep gene is involved in virus replication and integration. AAVs can infect a variety of cells.

Recombinant adeno-associated virus vector (rAAV) is derived from non-pathogenic wild-type adeno-associated virus. Due to its good safety, wide range of host cells (dividing and non-dividing cells), low immunogenicity, capability of long-term expression of exogenous genes in vivo and other characteristics, rAAV is regarded as one of the most promising gene transfer vectors and has been widely used in gene therapy and vaccine research worldwide. After more than 10 years of research, the biological characteristics of recombinant adeno-associated virus have been deeply understood, and a lot of data have been accumulated especially in the aspects of its application effects in various cells, tissues and in vivo experiments. In medical research, rAAV has been used in the research of gene therapy for various diseases (including in vivo and in vitro experiments). At the same time, as a characteristic gene transfer vector, it is also widely used in gene function research, disease model construction, and preparation of gene-knockout mice and other aspects.

In a preferred embodiment of the present invention, the vector is a recombinant AAV vector. AAVs are relatively small DNA viruses that can integrate into the genome of the cells that are infected by them in a stable and site-specific manner. They are capable of infecting a large range of cells without any effect on the growth, morphology or differentiation of the cells, and they do not seem to be involved in human pathology. The genome of AAV has been cloned, sequenced and characterized. AAV contains approximately 4,700 bases and an inverted terminal repeat (ITR) region of approximately 145 bases at each end, which region serves as the origin of replication of the virus. The rest of the genome is divided into two important regions with encapsidation functions: a left part of the genome containing the rep gene involved in viral replication and viral gene expression; and the right part of the genome containing the cap gene encoding the viral capsid protein.

AAV vectors can be prepared using standard methods in the art. Adeno-associated viruses of any serotype are suitable. Methods for purifying vectors can be found in, for example, U.S. Pat. Nos. 6,566,118, 6,989,264, and 6,995,006, the disclosures of which are incorporated herein by reference in their entirety. The preparation of hybrid vectors is described in, for example, PCT application No. PCT/US2005/027091, the disclosure of which is incorporated herein by reference in its entirety. The uses of AAV-derived vectors for transferring genes in vitro and in vivo have been described (see, for example, International Patent Application Publication Nos. WO91/18088 and WO93/09239; U.S. Pat. Nos. 4,797,368, 6,596,535 and 5,139,941, and European Patent No. 0,488,528, all of which are incorporated herein by reference in their entirety). These patent publications described various AAV-derived constructs in which the rep and/or cap genes are deleted and replaced by the gene of interest, and the uses of these constructs for transporting the gene of interest in vitro (entering cultured cells) or in vivo (directly entering organisms). Replication-deficient recombinant AAVs can be prepared by co-transfecting the following plasmids into a cell line infected with a human helper virus (such as adenovirus): plasmids containing the nucleic acid sequence of interest flanked by two regions of AAV inverted terminal repeat (ITR), and plasmids carrying AAV encapsidation genes (rep and cap genes). The resulting AAV recombinants are then purified by standard techniques.

In some embodiments, the recombinant vectors are subjected to encapsidation into viral particles (e.g., including but not limited to AAV1, AAV2, AAV3, AAV4, AAV5, AAV6, AAV7, AAV8, AAV9, AAV10, AAV11, AAV12, AAV13, AAV14, AAV15 and AAV16). Therefore, the present disclosure includes recombinant viral particles (called recombinant because they contain recombinant polynucleotides) containing any of the vectors described herein. Methods of producing such particles are known in the art and described in U.S. Pat. No. 6,596,535.

Nucleic Acid Coding Sequence

The technical problem to be solved by the present invention is to overcome the technical defects of low expression amount and poor therapeutic effects of the recombinant human type II mitochondrial dynein-like GTPase in the prior art. The purpose of the present invention is to provide an optimized gene sequence of recombinant human type II mitochondrial dynein-like GTPase. A gene of recombinant human type II mitochondrial dynein-like GTPase has an optimized CDS nucleotide sequence as shown in SEQ ID NO: 1 and a size of 2,775 bp, starting with codon ATG, and encoding 924 amino acids, wherein 1 to 288 bp is the coding sequence of OPA1-MIS, which encodes a peptide chain of 96 amino acids serving to guide the GTP protein to enter the mitochondria to exert its physiological functions; 289 to 2,772 bp codes a peptide chain of 828 amino acids which is served as a GTP functional protein; and the last 3 bp is a stop codon. Studies have found that the optimized OPA1 gene sequence (SEQ ID NO: 1) of the present invention makes the expression efficiency of OPA1 protein higher, and there are more OPA1 proteins that play physiological roles in the patient's optic ganglion cells.

The nucleotide sequence of the nucleic acid encoding the human type II mitochondrial dynein-like GTPase of the present invention is shown in SEQ ID NO: 1. In another preferred embodiment, the nucleotide sequence is ≥95%, preferably ≥98%, more preferably ≥99% identical to the nucleotide sequence shown in SEQ ID NO: 1. In the present invention, the nucleic acid encoding the human type II mitochondrial dynein-like GTPase is also called OPA1-optimized gene or OPA1-optimized nucleic acid.

The polynucleotides of the present invention may be in the form of DNA or RNA. In another preferred embodiment, the nucleotide is DNA. The forms of DNA include cDNA, genomic DNA or synthetic DNA. DNA can be single-stranded or double-stranded. DNA can be a coding strand or a non-coding strand. The nucleotide sequence of the present invention encodes the amino acid sequence shown in SEQ ID NO: 3. The OPA1-MIS signal peptide directs the protein to enter the mitochondria, and after being hydrolyzed by a protease, the mature OPA1 isoform 2 protein enters the mitochondria to play a role.

(SEQ ID NO.: 3)
MWRLRRAAVACEVCQSLVKHSSGIKGSLPLQKLHLVSRSIYHSHHPT

LKLQRPQLRTSPQQFSSLTNLPLRKLKFSPIKYGYQPRRNFWPARLA

TRLLKLRYLILGSAVGGGYTAKKTPDQWKDMIPDLSEYKWIVPDIVW

EIDEYIDFGSPEETAFRATDRGSESDKHFRKVSDKEKTDQLQEELLH

TQLKYQRILERLEKENKELRKLVLQKDDKGIHHRKLKKSLIDMYSEV

LDVLSDYDASYNTQDHLPRVVVVGDQSAGKTSVLEMLAQARIPPRGS

GEMMTRSPVKVTLSEGPHHVALFKDSSREFDLTKEEDLAALRHEIEL

RMRKNVKEGCTVSPETISLNVKGPGLQRMVLVDLPGVINTVTSGMAP

DTKETIFSISKAYMQNPNALILCIQDGSVDAERSIVTDLVSQMDPHG

RRTIFVLTKVDLAEKNVASPSRTQQILEGKLFPMKALGVFAVVTGKG

NSSESTEAIREVEEEFFQNSKLLKTSMLKAHQVTTRNLSLAVSDCFW

KMVRESVEQQADSFKATRFNLETEWKNNYPRLRELDRNELFEKAKNE

ILDEVISLSQVTPKHWEEILQQSLWERVSTHVIENIYLPAAQTMNSG

TFNTTVDIKLKQWTDKQLPNKAVEVAWETLQEEFSRFMTEPKGKEHD

DIFDKLKEAVKEESIKRHKWNDFAEDSLRVIQHNALEDRSISDKQQW

DAAIYFMEEALQARLKDTENAIENMVGPDWKKRWLYWKNRTQEQCVH

NETKNELEKMLKCNEEHPAYLASDEITTVRKNLESRGVEVDPSLIKD

TWHQVYRRHFLKTALNHCNLCRRGFYYYQRHFVDSELECNDVVLFWR

IQRMLAITANTLRQQLTNTEVRRLEKNVKEVLEDFAEDGEKKIKLLT

GKRVQLAEDLKKVREIQEKLDAFIEALHQEK

The nucleic acid sequence can be a DNA, an RNA, a cDNA or a PNA. The nucleic acid sequence can be genomic, recombinant or synthetic. The nucleic acid sequence can be isolated or purified. The nucleic acid sequence can be single-stranded or double-stranded. Preferably, the nucleic acid sequence will encode a photosensitive protein as described herein. Nucleic acid sequences can be derived by cloning, for example, using standard molecular cloning techniques including restriction digestion, ligation, and gel electrophoresis, as described in, for example, Sambrook et al. Molecular Cloning: A laboratory manual, Cold Spring Harbour Laboratory Press. The nucleic acid sequence may be isolated, for example, isolated using PCR technology. Isolation means the separation of a nucleic acid sequence from any impurities and from other nucleic acid sequences and/or proteins that are naturally found to associate with the nucleic acid sequences in its source. Preferably, it will also be free of a cell material, a culture medium or other chemicals from the purification/production processes. The nucleic acid sequence may be synthetic, for example, produced by direct chemical synthesis. The nucleic acid sequence can be provided as a naked nucleic acid, or can be provided in a complex with a protein or a lipid.

The full-length nucleotide sequence of the present invention or its fragments can usually be obtained by a PCR amplification method, a recombination method or an artificial synthesis method. For a PCR amplification method, primers can be designed according to a published relevant nucleotide sequence, especially the open reading frame sequence, and a commercially available cDNA library or a cDNA library prepared by a conventional method known to those skilled in the art can be used as a template; and a relevant sequence is obtained by amplification. When the sequence is relatively long, it is often necessary to perform two or more PCR amplifications, and then splice the individual amplified fragments together in the correct order. Currently, the DNA sequence encoding the polypeptide (or a fragment or derivative thereof) of the present invention can be obtained completely through chemical synthesis. The DNA sequence can then be introduced into various existing DNA molecules (or such as vectors) and cells known in the art.

The present invention also relates to a vector containing the polynucleotide of the present invention, and a host cell produced by genetic engineering using the vector or polypeptide-coding sequence of the present invention. The above-mentioned polynucleotide, vector or host cell may be isolated.

As used herein, "isolated" refers to the separation of a substance from its original environment (if it is a natural substance, the original environment refers to the natural environment). For example, a polynucleotide and a polypeptide in a natural state in living cells are not separated and purified, but the same polynucleotide or polypeptide is separated and purified when it is separated from other substances that coexist in the natural state.

In a preferred embodiment of the present invention, the nucleotide sequence is shown in SEQ ID NO: 1.

Once a relevant sequence is obtained, the recombination method can be used to obtain the relevant sequence on a large scale. This is usually done by cloning it into a vector, then transferring it into a cell, and then isolating the relevant sequence from the proliferated host cells by conventional methods.

In addition, the relevant sequence can also be synthesized using artificial synthesis methods especially when the fragment length is short. Usually, a fragment having a very long sequence can be obtained by firstly synthesizing multiple small fragments and then ligating them.

The method of amplifying DNA/RNA using PCR technology is preferably used to obtain the gene of the present invention. The primers used for PCR can be appropriately selected according to the sequence information of the present invention disclosed herein and can be synthesized by conventional methods. The amplified DNA/RNA fragments can be separated and purified by conventional methods such as gel electrophoresis.

The present invention also relates to a vector containing the polynucleotide of the present invention, a host cell produced by genetic engineering using the vector or protein coding sequence of the present invention, and a method for expressing OPA1 protein using the host cell through recombinant technology.

The host cells (such as mammalian cells) expressing the OPA1 protein of the present invention can be obtained using the polynucleotide sequence of the present invention through conventional recombinant DNA technology. Generally, the following step is included: transducing the polynucleotide described in the first aspect of the present invention or the vector described in the third aspect of the present invention into a host cell.

Methods well known to those skilled in the art can be used to construct the expression vector containing the DNA sequence encoding the polypeptide of the present invention and appropriate transcription/translation control signals. These methods include in vitro recombinant DNA technology, DNA synthesis technology and in vivo recombination technology. The DNA sequence can be effectively linked to an appropriate promoter in the expression vector to direct mRNA synthesis. The expression vector also comprises a ribosome binding site for translation initiation and a transcription terminator.

In addition, the expression vector preferably contains one or more selectable marker genes to provide phenotypic traits for selecting transformed host cells, such as dihydrofolate reductase for eukaryotic cell culture, neomycin resistance and green Fluorescent protein (GFP), or tetracycline or ampicillin resistance for E. coli.

The vector containing the appropriate DNA sequence described above and an appropriate promoter or control sequence can be used to transform an appropriate host cell so that it can express a polypeptide.

The host cell can be a prokaryotic cell, a lower eukaryotic cell or a higher eukaryotic cell, such as a mammalian cell (including human and non-human mammals). Representative examples are animal cells such as CHO, NSO, COS7 or 293 cells. In a preferred embodiment of the present invention, a 293T cell, a photoreceptor cell (including a cone cell and/or a rod cell), other visual cells (such as a bipolar cell) and a nerve cell are selected as the host cell. In another preferred embodiment, the host cell is selected from the group consisting of a rod cell, a cone cell, an on-bipolar cell, an off-bipolar cell, a horizontal cell, a ganglion cell, an amacrine cell or a combination thereof.

The transformation of the host cell using recombinant DNA can be performed by conventional techniques well known to those skilled in the art. When the host is a prokaryote such as Escherichia coli, a competent cell which is capable of absorbing DNA can be harvested after the exponential growth phase and treated by CaCl$_2$ method, in which the relevant steps used are well known in the art. Another method is to use MgCl$_2$. If necessary, transformation can also be performed by electroporation. When the host is an eukaryote, the following DNA transfection methods can be selected: the calcium phosphate co-precipitation method, and the conventional mechanical methods such as microinjection, electroporation, liposome packaging, etc.

The obtained transformants can be cultured by conventional methods to express the protein encoded by the gene of the present invention. Depending on the host cell used, the medium used in the culture can be selected from various conventional culture media. The culture is carried out under the conditions suitable for the growth of the host cell. When the host cell grows to an appropriate cell density, a suitable method (such as temperature conversion or chemical induction) is used to induce the selected promoter, and the cell is further cultured for a period of time.

In the above method, the polypeptide can be expressed in the cell or on the cell membrane or secreted out of the cell. If necessary, the protein can be separated and purified through various separation methods using its physical, chemical properties and other properties. These methods are well known to those skilled in the art. Examples of these methods include, but are not limited to: conventional renaturation treatment, treatment with protein precipitation agent (salting out method), centrifugation, cell breaking via osmosis, ultra-treatment, ultra-centrifugation, molecular sieve chromatography (gel filtration), adsorption chromatography, ion exchange chromatography, high performance liquid chromatography (HPLC) and various other liquid chromatography techniques and the combinations of these methods.

Sequence Optimization

In the present invention, an optimized coding sequence of recombinant human type II mitochondrial dynein-like GTPase that is particularly suitable for expression in mammalian cells is provided, and the coding sequence is shown in SEQ ID NO: 1.

As used herein, the "optimized OPA1 coding sequence" and "optimized OPA1 coding gene" refer to a nucleotide sequence for encoding the recombinant human type II mitochondrial dynein-like GTPase, and the nucleotide sequence encodes the amino acid sequence shown in SEQ ID NO: 3.

In the present invention, the wild DNA coding sequence (unoptimized DNA coding sequence) of the recombinant human type II mitochondrial dynein-like GTPase is shown in SEQ ID NO: 2. The expression amount of the unoptimized wild DNA coding sequence is very low.

Wild Homo sapiens: OPA1 isoform2 CDS 2775 bp (SEQ ID NO.: 2)
ATGTGGCGACTACGTCGGGCCCCTGTGGCCTGTGAGGTCT

GCCAGTCTTTAGTGAAACACAGCTCTGGAATAAAAGGAAGTTTACC

ACTACAAAAACTACATCTCGTTTCACGAAGCATTTATCATTCACAT

CATCCTACCTTAAAGCTTCAACGACCCCAATTAAGGACATCCTTTC

AGCAGTTCTCTTCTCTGACAAACCTTCCTTTAGGTAAACTGAAATT

CTCTCCAATTAAATATGCCTACCAGCCTCGCAGGAATTTTTGGCCA

GCAAGATTAGCTACGAGACTCTTAAAACTTCCCTATCTCATACTAG

GATCGGCTGTTGGGGGTGGCTACACACCCAAAAAGACTTTTGATCA

GTGGAAAGATATGATACCGGACCTTAGTGAATATAAATGGATTGTG

CCTGACATTGTGTGGGAAATTGATGAGTATATCGATTTTGGTTCTC

CGGAAGAAACGGCGTTTAGAGCAACAGATCGTGGATCTGAAAGTGA

CAAGCATTTTAGAAAGGTGTCAGACAAAGAGAAAATTGACCAACTT

CAGGAAGAACTTCTGCACACTCAGTTGAAGTATCAGAGAATCTTGG

AACGATTAGAAAAGGAGAACAAAGAATTGAGAAAATTAGTATTGCA

GAAAGATGACAAAGGCATTCATCATAGAAAGCTTAAGAAATCTTTG

ATTGACATGTATTCTGAAGTTCTTGATGTTCTCTCTGATTATGATG

CCAGTTATAATACGCAAGATCATCTGTCACGGGTTGTTGTGGTTGG

AGATCAGAGTGCTGGAAAGACTAGTGTGTTGGAAATGATTGCCCAA

GCTCGAATATTCCCAAGAGGATCTGGGGAGATGATGACACGTTCTC

CAGTTAAGGTGACTCTGAGTGAAGGTCCTCACCATGTGGCCCTATT

TAAAGATACTTCTCGGGAGTTTGATCTTACCAAAGAAGAAGATCTT

GCAGCATTAAGACATGAAATAGAACTTCGAATGAGGAAAAATGTGA

AAGAAGGCTGTACCGTTAGCCCTGAGACCATATCCTTAAATGTAAA

AGGCCCTGGACTACAGAGGATGGTGCTTGTTGACTTACCAGGTGTG

ATTAATACTGTGACATCAGGCATGGCTCCTGACACAAAGGAAACTA

TTTTCAGTATCAGCAAAGCTTACATGCAGAATCCTAATGCCATCAT

ACTGTGTATTCAAGATGGATCTGTGGATGCTGAACGCAGTATTGTT

ACAGACTTGGTCAGTCAAATGGACCCTCATGGAAGGAGAACCATAT

TCGTTTTGACCAAAGTAGACCTGGCAGAGAAAAATGTAGCCAGTCC

AAGCAGGATTCAGCAGATAATTGAAGGAAAGCTCTTCCCAATGAAA

-continued

```
GCTTTAGGTTATTTTGCTGTTGTAACAGGAAAAGGGAACAGCTCTG
AAAGCATTGAAGCTATAAGAGAATATGAAGAAGAGTTTTTTCAGAA
TTCAAAGCTCCTAAAGACAAGCATGCTAAAGGCACACCAAGTGACT
ACAAGAAATTTAAGCCTTGCAGTATCAGACTGCTTTTGGAAAATGG
TACGAGAGTCTGTTGAACAACAGGCTGATAGTTTCAAAGCAACACG
TTTTAACCTTGAAACTGAATGGAAGAATAACTATCCTCGCCTCCGG
GAACTTGACCGGAATGAACTATTTGAAAAACCTAAAAATGAAATCC
TTGATGAAGTTATCAGTCTGAGCCAGGTTACACCAAAACATTGGGA
GGAAATCCTTCAACAATCTTTGTGGGAAAGAGTATCAACTCATGTG
ATTGAAAACATCTACCTTCCAGCTGCGCAGACCATGAATTCAGGAA
CTTTTAACACCACAGTGGATATCAAGCTTAAACAGTGGACTGATAA
ATGACATATTTGATAAACTTAAAGAGGCTGTTAAGGAAGAAAGTAT
TAAACGACACAAGTGGAATGACTTTGCGGAGGACAGCTTGAGGGTT
ATTCAACACAATGCTTTGGAAGACCGATCCATATCTGATAAACAGC
AATGGGATGCAGCTATTTATTTTATGGAAGAGGCTCTGCAGGCTCG
TCTCAAGGATACTGAAAATGCAATTGAAAACATGGTGGGTCCAGAC
TGGAAAAAGAGGTGGTTATACTGGAAGAATCGGACCCAAGAACAGT
GTGTTCACAATGAAACCAAGAATGAATTGGAGAAGATGTTGAAATG
TAATGAGGAGCACCCAGCTTATCTTGCAAGTGATGAAATAACCACA
GTCCGGAAGAACCTTGAATCCCGAGGAGTAGAAGTAGATCCAAGCT
TGATTAAGGATACTTGGCATCAAGTTTATAGAAGACATTTTTTAAA
AACAGCTCTAAACCATTGTAACCTTTGTCGAAGAGGTTTTTATTAC
TACCAAAGGCATTTTGTAGATTCTGAGTTGGAATGCAATGATGTGG
TCTTGTTTTGGCGTATACAGCGCATGCTTGCTATCACCGCAAATAC
TTTAAGGCAACAACTTACAAATACTGAAGTTAGGCGATTAGAGAAA
AATGTTAAAGAGGTATTGGAAGATTTTGCTGAAGATGGTGAGAAGA
AGATTAAATTGCTTACTGGTAAACCCGTTCAACTGGCGGAAGACCT
CAAGAAAGTTAGAGAAATTCAAGAAAAAGTTGATGCTTTCATTGAA
GCTCTTCATCAGGAGAAATAA
```

The present invention has optimized the sequence fragments that affect gene expression and protein localization, in which the optimizations of these sequence fragments include, but are not limited to, codon usage bias; elimination of secondary structures that are not conducive to expression (such as hairpin structure); and changing the GC content, the content of CpG dinucleotide, the secondary structure of mRNA, cryptic splice sites, early polyadenylation sites, internal ribosome entry and binding sites, negative CpG islands, unstable regions of RNA, repeat sequences (direct repeat sequences, inverted repeat sequences, etc.) and restriction sites that may affect cloning. A specially optimized DNA coding sequence as shown in SEQ ID NO: 1 is finally obtained through analysis and experimental screening. This sequence is specially optimized, so the transcription level thereof is slightly increased and the expression amount thereof is significantly increased. The similarity between the specially optimized coding sequence shown in SEQ ID NO: 1 and the wild coding sequence shown in SEQ ID NO: 2 is 72.25% (2005/2775), as shown in FIG. 1.

Optimized *Homo sapiens*: OPA1 isoform2 CDS 2775 bp (SEQ ID NO.: 1)
```
ATGTGGCGCCTGCGCCGCGCCGCCGTGGCCTGCGAGGTGTG
CCAGAGCCTGGTGAAGCACAGCAGCGGCATCAAGGGCAGCCTGCCC
CTGCAGAAGCTGCACCTGGTGAGCCGCAGCATCTACCACAGCCACC
ACCCCACCCTGAAGCTGCAGCGCCCCCAGCTGCGCACCAGCTTCCA
GCAGTTCAGCAGCCTGACCAACCTGCCCCTGCGCAAGCTGAAGTTC
AGCCCCATCAAGTACGGCTACCAGCCCCGCCGCAACTTCTGGCCCG
CCCGCCTGGCCACCCGCCTGCTGAAGCTGCGCTACCTGATCCTGGG
CAGCGCCGTGGGCGGCGGCTACACCGCCAAGAAGACCTTCGACCAG
TGGAAGGACATGATCCCCGACCTGAGCGAGTACAAGTGGATCGTGC
CCGACATCGTGTGGGAGATCGACGAGTACATCGACTTCGCCAGCCC
CGAGGAGACCGCCTTCCGCGCCACCGACCGCGGCAGCGAGAGCGAC
AAGCACTTCCGCAAGGTGAGCGACAAGGAGAAGATCGACCAGCTGC
AGGAGGAGCTGCTGCAGACCCAGCTGAAGTACCAGCGCATCCTGGA
GCGCCTGGAGAAGGAGAACAAGGAGCTGCGCAAGCTGGTGCTGCAG
AAGGACGACAAGGGCATCCACCACCGCAAGCTGAAGAAGAGCCTGA
TCGACATGTAGAGCGAGGTGCTGGACGTGCTCAGCGACTACGACGC
CAGCTACAACACCCAGGACCACCTGCCCCGCGTGGTGGTGGTGGGC
GACCAGAGCGCCGGCAAGACCAGCGTGCTGGAGATGATCGCCCAGG
CCCGCATCTTCCCCCGCGGCAGCGGCGAGATGATGACCCGCAGCCC
CGTGAAGGTGACCCTGAGCGAGGGCCCCCACCACGTGGCCCTGTTC
AAGGACAGCAGCCGCGAGTTCGACCTGACCAAGGAGGAGGACCTGG
CCGCCCTGCGCCACGAGATCGAGCTGCGCATGCGCAAGAACGTGAA
GGAGGGCTGCACCGTGAGCCCCGAGACCATCAGCCTGAACGTGAAG
GGCCCCGGCCTGCAGCGCATGGTGCTGGTGGACCTGCCCGGCGTGA
TCAACACCGTGACCAGCGGCATGGCCCCCGACACCAAGGAGACCAT
CTTCAGCATCAGCAAGGCCTACATGCAGAACCCCAACGCCATCATC
CTGTGCATCCAGGACGGCAGCGTGGACGCCGAGCGCAGCATCGTGA
CCGACCTGGTGAGCCAGATGGACCCCCACGGCCGCCGCACCATCTT
CGTGCTGACCAAGGTGGACCTGGCCGAGAAGAACGTGGCCAGCCCC
AGCCGCATCCAGCAGATCATCGAGGGCAAGCTGTTCCCCATGAAGG
CCCTGGGCTACTTCGCCGTGGTGACCGGCAAGGGCAACAGCAGCCA
GAGCATCGAGGCCATCCCCGAGTACGAGGAGCACTTCTTCCAGAAC
AGCAAGCTGCTGAAGACCAGCATGCTGAAGGCCACCAGGTGACCA
CCCGCAACCTGAGCCTGGCCGTGAGCGACTGCTTCTGGAAGATGGT
GCCCGAGAGCGTGGAGCAGCAGGCCGACAGCTTCAAGGCCACCCGC
TTCAACCTGGAGACCGAGTGCAAGAACAACTACCCCCGCCTGCGCG
AGCTGGACCGCAACGAGCTGTTCGAGAAGGCCAAGAACGAGATCCT
GGACGAGGTCATCAGCCTGAGCCAGGTGACCCCCAAGCACTGGGAG
GAGATCCTGCAGCAGAGCCTGTGGGAGCGCGTGAGCACCCACGTGA
```

-continued

```
TCGAGAACATCTACCTGCCCGCCGCCCAGACCATGAACAGCGGCAC

CTTCAACACCACCGTGGACATCAAGCTGAAGCAGTGGACCGACAAG

CAGCTGCCCAACAAGGCCGTGGAGGTGGCCTGGGAGACCCTGCAGG

AGGAGTTCAGCCGCTTCATGACCGAGCCCAAGGGCAAGGAGCACGA

CGACATCTTCGACAAGCTGAAGGAGGCCGTGAAGGAGGAGAGCATC

AAGCGCCAGAAGTGGAACGACTTCGCCGAGGACAGCCTGCGCGTGA

TCCAGCACAACGCCCTGGAGGACCGCAGCATCAGCGACAAGCAGCA

GTGGGACGCCGCCATCTACTTCATGGAGGAGGCCCTGCAGGCCCGC

CTGAAGGACACCGAGAACGCCATCGAGAACATGGTGGGCCCCGACT

GGAAGAAGCGCTGGCTGTACTGGAAGAACCGCACCCAGCAGCAGTG

CGTGCACAACGAGACCAAGAACGAGCTGGAGAAGATGCTGAAGTGC

AACGAGGAGCACCCCGCCTACCTGGCCAGCGACGAGATCACCACCG

TGCGCAAGAACCTGGAGAGCCGCGGCGTGGAGGTGGACCCCAGCCT

GATCAAGGACACCTGGCACCAGGTGTACCACCGCCACTTCCTGAAG

ACCGCCCTGAACCACTGCAACCTGTGCCGCCGCGGCTTCTACTACT

ACCAGCGCCACTTCGTGGACAGCGAGCTGGAGTGCAACGACGTGGT

GCTGTTCTGCCGCATCCAGCGCATGCTGGCCATCACCGCCAACACC

CTGCGCCAGCAGCTGACCAACACCGAGGTGCGCCGCCTGGAGAAGA

ACGTGAAGGAGGTGCTGGAGGACTTCGCCGAGGACGGCGAGAAGAA

GATCAAGCTGCTGACCGGCAAGCGCGTGCAGCTGGCCGAGGACCTG

AAGAAGGTGCGCGAGATCCAGGAGAAGCTGGACGCCTTCATCGAGG

CCCTGCACCAGGAGAAGTAA
```

Fusion Nucleic Acid

The present invention also provides a fusion nucleic acid comprising the nucleic acid sequence encoding the human type II mitochondrial dynein-like GTPase described in the first aspect of the present invention.

As used herein, "fusion nucleic acid" refers to a nucleic acid formed by ligating two or more nucleotide sequences from different sources, or a nucleic acid formed by ligating two or more nucleotide sequences from the same source but not ligating to each other in their natural positions.

In another preferred embodiment, the fusion nucleic acid further comprises a sequence selected from the group consisting of a UTR sequence, a promoter sequence or a combination thereof.

Preferably, the fusion nucleic acid has a UTR sequence operably linked to the nucleic acid encoding the human type II mitochondrial dynein-like GTPase.

In another preferred embodiment, the UTR sequence includes a 3'-UTR and/or a 5'-UTR.

In another preferred embodiment, the UTR sequence contains a polyA sequence for stabilizing the structure.

In another preferred embodiment, the fusion nucleic acid has a structure of formula I from the 5'-end to the 3'-end:

Z1-Z2-Z3    (I)

wherein each "-" is independently a bond or a nucleotide linker sequence;

Z1 is a 5'-UTR sequence;

Z2 is the nucleotide sequence as described in the first aspect of the present invention; and Z3 is a 3'-UTR sequence.

Expression Vector and Host Cell

The present invention also provides an expression vector for OPA1 protein, which contains the optimized OPA1 coding sequence of the present invention.

With the provided sequence information, a skilled person in the art can use available cloning techniques to generate nucleic acid sequences or vectors suitable for transduction into cells.

Preferably, the nucleic acid sequence encoding the OPA1 protein is provided as a vector, preferably an expression vector. Preferably, it can be provided as a gene therapy vector preferably suitable for transduction and expression in retinal target cells. The vector can be viral or non-viral (e.g., a plasmid). Viral vectors include those derived from the following viruses: adenovirus, adeno-associated virus (AAV) including mutant forms, retrovirus, lentivirus, herpes virus, vaccinia virus, MMLV, GaLV, simian immunodeficiency virus (SIV), HIV, poxvirus and SV40. Preferably, the viral vectors are replication defective, although it is envisaged that they can be replication deficient, they are capable of replication or conditional replication. Viral vectors can usually maintain an extrachromosomal state without integrating into the genome of target retinal cells. The preferred viral vector for introducing the nucleic acid sequence encoding OPA1 protein into retinal target cells is AAV vector, such as a self-complementary adeno-associated virus (scAAV). Selective targeting can be achieved using a specific AAV serotype (AAV serotype 2 to AAV serotype 12) or a modified version of any one of these serotypes (including AAV 4YF and AAV 7m8 vectors).

The viral vector can be modified to delete any unnecessary sequences. For example, as for AAV, the virus can be modified to delete all or part of the IX gene, E1a and/or E1b genes. For wild-type AAV, if there is no helper virus such as adenovirus, its replication efficiency is very low. For a recombinant adeno-associated virus, preferably, the replication gene and capsid gene are provided in trans (in a pRep/Cap plasmid), and only the 2ITR of the AAV genome is retained and packaged into the virions, while the required adenovirus genes are provided by an adenovirus or another plasmid. Similar modifications can also be made to a lentiviral vector.

A viral vector has the ability of entering a cell. However, a non-viral vector such as a plasmid can be complexed with an agent to facilitate the uptake of the viral vector by a target cell. Such agents include polycationic agents. Optionally, a delivery system such as a liposome-based delivery system may be used. The vector for use in the present invention is preferably suitable for use in vivo or in vitro, and is preferably suitable for use in human beings.

The vector will preferably contain one or more regulatory sequences to direct the expression of the nucleic acid sequence in retinal target cells. The regulatory sequence may include a promoter, an enhancer, a transcription termination signal, a polyadenylation sequence, an origin of replication, a nucleic acid restriction site and a homologous recombination site operably linked to the nucleic acid sequence. The vector may also include a selectable marker, for example, to determine the expression of the vector in a growth system (e.g., a bacterial cell) or in retinal target cells.

"Operably linked" means that a nucleic acid sequence is functionally related to the sequence to which it is operably linked so that they are linked in such a way that they affect each other's expression or functions. For example, a nucleic acid sequence operably linked to a promoter will have an expression pattern affected by the promoter.

The promoter mediates the expression of the nucleic acid sequence to which it is linked. The promoter can be constitutive or inducible. A promoter can direct the ubiquitous expression in inner retinal cells or neuron-specific expression. In the latter case, the promoter can direct cell type-specific expression, for example, the optic ganglion cells. Suitable promoters will be known to those skilled in the art. For example, a suitable promoter can be selected from the group consisting of: L7, thy-1, recoverin, calbindin, human CMV, GAD-67, chicken (3-actin, hSyn, Grm6, and Grm6 enhancer SV40 fusion protein. Targeting can be achieved using a cell-specific promoter, such as Grm6-SV40 for selective targeting to the optic nerve cells. The Grm6 promoter is a fusion of the 200-base pair enhancer sequence of the Grm6 gene and the SV40 eukaryotic promoter, and the Grm6 gene encodes mGluR6, a metabotropic glutamate receptor specific for optic nerve cells. Preferred sources of the Grm6 gene are mice and human beings. Ubiquitous expression can be achieved using a pan-neuronal promoter, examples of which are known and available in the art. Such an example is CAG. CAG promoter is a fusion of CMV early enhancer and chicken (3-actin promoter.

An example of a suitable promoter is the immediate-early cytomegalovirus (CMV) promoter sequence. The promoter sequence is a strong constitutive promoter sequence capable of driving high-level expression of any polynucleotide sequence to which it is operably linked. Another example of a suitable promoter is elongation growth factor-1α (EF-1α). However, other constitutive promoter sequences can also be used, including but not limited to, simian virus 40 (SV40) early promoter, mouse mammary tumor virus (MMTV), human immunodeficiency virus (HIV) long terminal repeat (LTR) promoter, MoMuLV promoter, avian leukemia virus promoter, Epstein-Barr virus immediate-early promoter, Rous sarcoma virus promoter, and human gene promoter, such as but not limited to actin promoter, myosin promoter, heme promoter and creatine kinase promoter. Further, the present invention should not be limited to the applications of constitutive promoters. Inducible promoters are also considered part of the invention. The use of an inducible promoter provides a molecular switch that can turn on the expression of a polynucleotide sequence operably linked to an inducible promoter when such an expression is desired, or turn off the expression when the expression is not desired. Examples of inducible promoters include, but are not limited to, metallothionein promoters, glucocorticoid promoters, progesterone promoters and tetracycline promoters.

Many expression vectors can be used to express OPA1 protein in mammalian cells (preferably human cells, more preferably human optic nerve cells or photoreceptor cells). Adeno-associated virus is preferably used as the expression vector in the present invention.

The present invention also provides a method for constructing an adeno-associated virus vector for the recombinant application of the gene of recombinant human type II mitochondrial dynein-like GTPase, which method can quickly and easily construct a recombinant adeno-associated virus vector carrying the gene of recombinant human type II mitochondrial dynein-like GTPase, which is packaged to obtain a replication-defective adeno-associated virus vector.

The present invention also provides a host cell for expressing the OPA1 protein. Preferably, the host cell is a mammalian cell (preferably a human cell, more preferably a human optic nerve cell or a photoreceptor cell) which increases the expression amount of the OPA1 protein.

Preparations and Compositions

The present invention provides a preparation or a composition which contains (a) the vector according to the third aspect of the present invention, and (b) a pharmaceutically acceptable carrier or excipient.

In another preferred embodiment, the pharmaceutical preparation is used for treating eye diseases.

In another preferred embodiment, the pharmaceutical preparation is used for treating hereditary optic neuropathy, preferably autosomal dominant optic atrophy (ADOA).

An "active ingredient" in the pharmaceutical composition described in the present invention refers to the vector of the present invention, such as a viral vector (including an adeno-associated virus vector). The "active ingredients", preparations and/or compositions described in the present invention can be used for treating eye diseases. "Safe and effective amount" means that the amount of the active ingredient can obviously improve pathogenic conditions or symptoms without producing serious side effects. "Pharmaceutically acceptable carrier or excipient" means one or more compatible solid or liquid fillers or gel substances which are suitable for human use and moreover must have sufficient purity and sufficiently low toxicity. "Compatibility" herein means that the individual components in the composition can be incorporated with the active ingredients of the present invention and incorporated with one another without obviously reducing the drug effects of the active ingredients.

The composition may be a liquid or a solid, such as powder, gel or paste. Preferably, the composition is liquid, preferably liquid for injection. Suitable excipients will be known to those skilled in the art.

In the present invention, the carrier can be administered to the eye by subretinal administration or intravitreal administration. In either mode of administration, the carrier is preferably provided as liquid for injection. Preferably, the liquid for injection is provided as a capsule or a syringe.

The examples of the pharmaceutically acceptable carrier include cellulose and derivatives thereof (such as sodium carboxymethylcellulose, sodium ethyl cellulose, cellulose acetate and the like), gelatin, talc, solid lubricant (such as stearic acid, magnesium stearate), calcium sulfate, a vegetable oil (such as soybean oil, sesame oil, peanut oil, olive oil and the like), polyols (such as propylene glycol, glycerine, mannitol, sorbitol and the like), an emulsifying agent (such as Tween®), a wetting agent (such as sodium lauryl sulfate), a colorant, a flavoring agent, a stabilizing agent, an antioxidant, a preservative, pyrogen-free water and the like.

The composition may include a physiologically acceptable sterile aqueous or non-aqueous solution, a dispersion, a suspension or an emulsion, and a sterile powder for reconstitution into sterile solution or dispersion for injection. Suitable aqueous and non-aqueous carriers, diluents, solvents or excipients include water, ethanol, polyols and suitable mixtures thereof.

The nucleic acid or fusion nucleic acid encoding OPA1 provided by the present invention can produce OPA1 protein or OPA1 fusion protein in vitro or in vivo, and the fusion protein or the preparation containing the fusion protein can be used to prepare a drug for treating autosomal dominant optic atrophy (ADOA).

The optimized nucleic acid that encodes human type II mitochondrial dynein-like GTPase has a higher expression amount, thereby translating more OPA1 protein, and the MIS sequence in the optimized OPA1 protein can accurately make the GTP functional protein enter mitochondria, and therefore there are more GTPase being transfected into mitochondria. A medicament containing the nucleic acid of the present invention is injected into the vitreous cavity of the eye of a rabbit, and the medicament maintains activity in the vitreous cavity and the nucleic acid is transfected to optic nerve cells. As compared with the prior art, the optimized nucleic acid encoding OPA1 expresses more OPA1 protein, which can better treat autosomal dominant optic atrophy (ADOA).

As Compared with the Prior Art, the Present Invention Mainly has the Following Advantages:

1. The gene coding sequence of the recombinant human type II mitochondrial dynein-like GTPase (OPA1) of the present invention has been specially optimized, including the optimization of the MIS coding sequence and the coding sequence of GTPase domain in OPA1 As compared with the unoptimized DNA coding sequence of OPA1, the expression amount is significantly increased, and more OPA1 protein is transfected into mitochondria. The optimized sequence ensures that the OPA1 protein is expressed at a significantly increased amount and has high biological activity.

2. The optimized OPA1 encoding gene (SEQ ID NO: 1) or the fusion nucleic acid in the present invention can effectively treat autosomal dominant optic atrophy (ADOA) with good safety.

3. The present invention provides a non-human mammalian model of ADOA based on the inactivation of the gene of type II mitochondrial dynein-like GTPase, which model exhibits the pathological manifestations similar to autosomal dominant optic atrophy (ADOA), including reduced content of retinal ATP and apoptotic changes of mitochondria, and can be used for the experimental research, evaluation or drug screening for autosomal dominant optic atrophy (ADOA).

4. The rAAV2-hOPA1 recombinant adeno-associated virus provided by the present invention has significant and efficient improvement effects on the pathological conditions of the model mice of point mutation of ADOA (autosomal dominant optic atrophy), and can provide continuous improvement effects; and it can completely and effectively reverse the impacts of the disease in the model mice 3 months after a single administration.

The present invention is further illustrated in connection with particular examples as follows. It should be understood that these examples are merely illustrative of the present invention and are not intended to limit the scope of the present invention. The experimental methods with specific conditions not specified in the following examples, are generally in accordance with conventional conditions, such as the conditions described in Sambrook et al., Molecular Cloning: A Laboratory Manual (New York: Cold Spring Harbor Laboratory Press, 1989), or conditions recommended by the manufacturer. All percentages and parts are calculated by weight unless otherwise indicated.

Example 1 Construction of Recombinant Adeno-Associated Virus Vector for the Gene of Recombinant Human Type II Mitochondrial Dynein-Like GTPase and its Virus Packaging and Purification Methods 1. Construction of Recombinant Adeno-Associated Virus Vector Containing the Gene of Human Type II Mitochondrial Dynein-Like GTPase 1) Vector Construction Two restriction digestion sites Kpn I and Sal I were added to the specially optimized gene of recombinant human type II mitochondrial dynein-like GTPase (SEQ ID NO: 1); alternatively, primers were designed according to this novel gene to amplify the gene by PCR to give a product, and the product and a pSNaV plasmid vector were respectively subjected to double digestion with Kpn I and Sal I; and the digested products were recovered and ligated overnight with T4 DNA Ligase, and the ligation products were transformed into competent cells to obtain recombinant pSNaV/rAAV2/2-hOPA1 isoform 2 (FIG. 2).

2) Screening and Identification of Recombinants

On LB plates after being cultured at 37° C., blue plaques and white plaques appeared, and the white plaques were the recombinant clones. The white colonies were picked out and added to a LB liquid medium containing 100 mg/L of Amp and cultured at 37° C. at 200 rpm for 8 h. Plasmids were extracted from the cultured bacterial suspension, with the plasmid extraction steps referring to the instructions from Biomiga. 1 µL of plasmid was taken as the template, and the specific primers were:

1F:
                                            (SEQ ID NO.: 4)
5'-ATGTGGCGACTACGTCG-3';

1R:
                                            (SEQ ID NO.: 5)
5'-TTATTTCTCCTGATGAAGAG-3';

Procedures for PCR Amplification

| Procedures | 1 Temperature | Time | 2 Temperature | Time |
|---|---|---|---|---|
| Predenaturation | 95° C. | 3 min | 95° C. | 3 min |
| Denaturation | 94° C. | 30 s | 94° C. | 30 s |
| Annealing | 60° C. | 30 s | 58° C. | 35 s |
| Extension | 72° C. | 60 S | 72° C. | 60 S |
| Repair extension | 72° C. | 8 min | 72° C. | 8 min |
| Number of cycles | 25 C | | 25 C | |

The PCR product was detected by electrophoresis, and the result was shown in FIG. 3. A band of interest with a size of about 3000 bp was obtained. The identification results showed that the clone contained the gene of interest.

Figure 4:
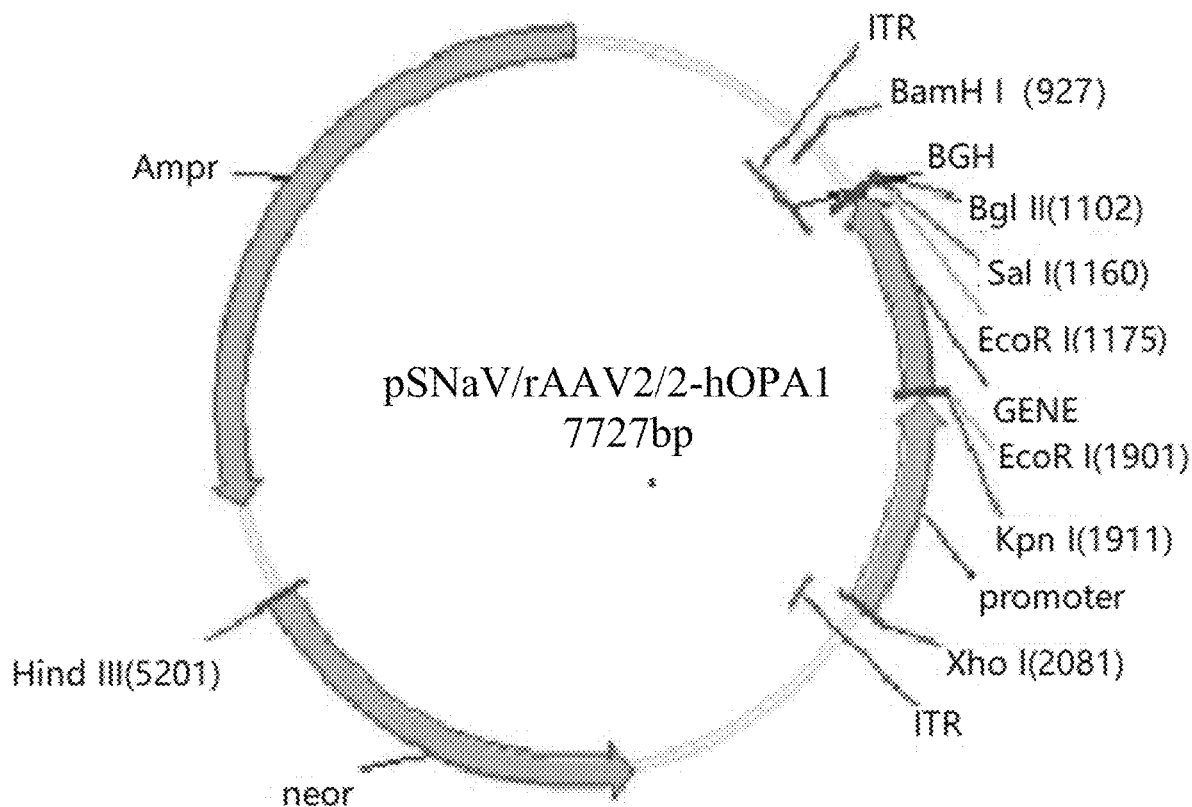
FIG. 4 shows the schematic diagram of the structure of the recombinant adeno-associated virus plasmid pSNaV/rAAV2/2-hOPA1.

3) Preservation of Bacterial Suspension, PCR Amplification and Fragment Sequencing Thereof 1 mL of the identified bacterial suspension was pipetted and mixed with sterilized glycerol at a ratio of 1:3, and stored at −80° C.; the bacterial suspension was subjected to sequencing; the sequence obtained by sequencing was aligned with the gene of recombinant human type II mitochondrial dynein-like GTPase, and a recombinant adeno-associated virus plasmid pSNaV/rAAV2/2-hOPA1 with the correct sequence was successfully obtained (FIG. 4).

2. Enveloping of rAAV2/2-hOPA1 Isoform 2 Recombinant Adeno-Associated Virus

1) On the day before transfection, 293T cells were inoculated in a 225 cm² cell culture flask with a seeding density of 3.0×10⁷ cells/mL, wherein the medium was DMEM+10% bovine serum, and cultured in an incubator containing 5% $CO_2$ at 37° C. overnight.

2) The medium was changed on the day of transfection, and culture was continued with a fresh DMEM medium containing 10% bovine serum. The culture medium was discarded when the cells had grown to 80-90%, and transfection was carried out using PlasmidTrans II (VGTC) transfection kit. The specific steps were as follows:

(a) plasmids pAdHelper, pAAV-r2c5 and pSNaV-hOPA1 were taken from each transfection flask and mixed with DMEM+PlasmidTrans II (VGTC) (transfection reagent) according to the required ratios in a 1.5 mL sterile Ep tube, numbered as reagent A, and then the reagent A was kept still at room temperature for 10-15 min;

(b) the reagent A was mixed with 30 mL of DMEM+10% bovine serum, numbered as reagent B;

(c) the reagent B was evenly added into a cell culture flask, and culture was continued in an incubator containing 5% $CO_2$ at 37° C.;

(d) complete medium (DMEM+10% bovine serum) was added for change 16 h after transfection.

3) cells were collected 48 h after transfection.

4) the collected cells were suspended in PBS, and frozen-thawed repeatedly 3 times.

3. Purification and Concentration of rAAV2/2-hOPA1 Isoform 2 Virus

Three steps of chloroform treatment-PEG/NaCl precipitation-chloroform extraction were used to separate, concentrate and purify rAAV2/2-hOPA1 virus. Total recovery rate=number of virus particles in final product/number of virus particles in starting material.

4. Verification of Purity and Titer of Viruses

SDS-PAGE separating gel and stacking gel were loaded, wherein the concentration of the separating gel is 10%. 15 μg of samples were respectively added to each sample well. After electrophoresis, the gel was stained with Coomassie Brilliant Blue and destained with a corresponding destaining solution until clear bands with low background appeared (FIG. 5).

Figure 5:
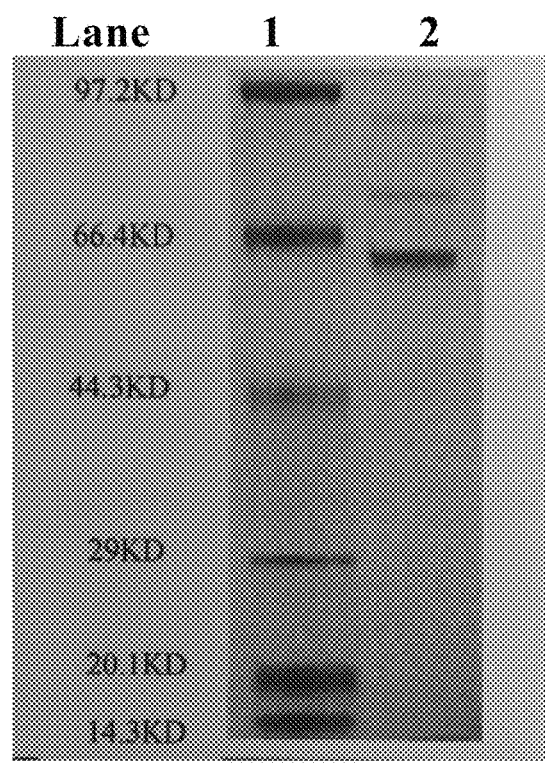
FIG. 5 shows the results of Coomassie Brilliant Blue staining for detecting the purity of rAAV2/2-hOPA1 isoform 2 by SDS-PAGE electrophoresis. Among them, lane 1: protein marker; lane 2: rAAV2/2-hOPA1 isoform 2.

The results were shown in FIG. 5, VP1/VP2/VP3=1:1:10, the bands were clear and the ratio was normal, there was no impurity band, and the purity was above 99%.

As for the determination of the titer of rAAV2/2-hOPA1 isoform 2, a fluorescence quantitative PCR method was employed to determine the physical titer of rAAV2/2-hOPA1 isoform 2.

Experimental materials: SYBRII (takara); primers for fragment of interest (20 μM); plasmid of interest for packaging virus (known concentration); virus to be determined; PCR eight-strip tube (Bio-red).

Experimental method: template 1 μl, SYBRII 7 μl, primer 1 0.25 μl, and primer 2 0.25 μl were taken, and nuclease-free water was added up to 14 μl.

PCR reaction conditions: pre-denaturation: 95° C. 10 min; cycles: 95° C. 15 sec, 60° C. 1 min.

Finally, it was determined that the genome titer was $1\times10^{12}$ vg/mL.

Example 2: Experiment on Effects of rAAV2/2-hOPA1 Recombinant Adeno-Associated Virus on ADOA (Autosomal Dominant Optic Atrophy)

1. Injection into Vitreous Cavity of Eye of Rabbit

Twenty-four rabbits were divided into 3 groups, including an experimental group A, an experimental group B and a control group. 50 μl of $1\times10^{12}$ vg/mL rAAV2/2-optimized hOPA1 isoform 2, rAAV2/2-original hOPA1 isoform 2 and rAAV-ZsGreen were respectively drawn, and injected into vitreous cavity by puncturing the flat part of ciliary body at 3 mm away from the corneal limbus.

2. Slit Lamp, Intraocular Pressure, Fundus Photography Examinations

Two groups of rabbits underwent slit lamp and intraocular pressure examinations respectively at day 1, day 3, day 7 and day 30 after the operation. All rabbits had no obvious abnormalities, no conjunctival congestion and secretions, no endophthalmitis, and no increase in intraocular pressure as shown in fundus photographs one month after the operation.

Figure 6:
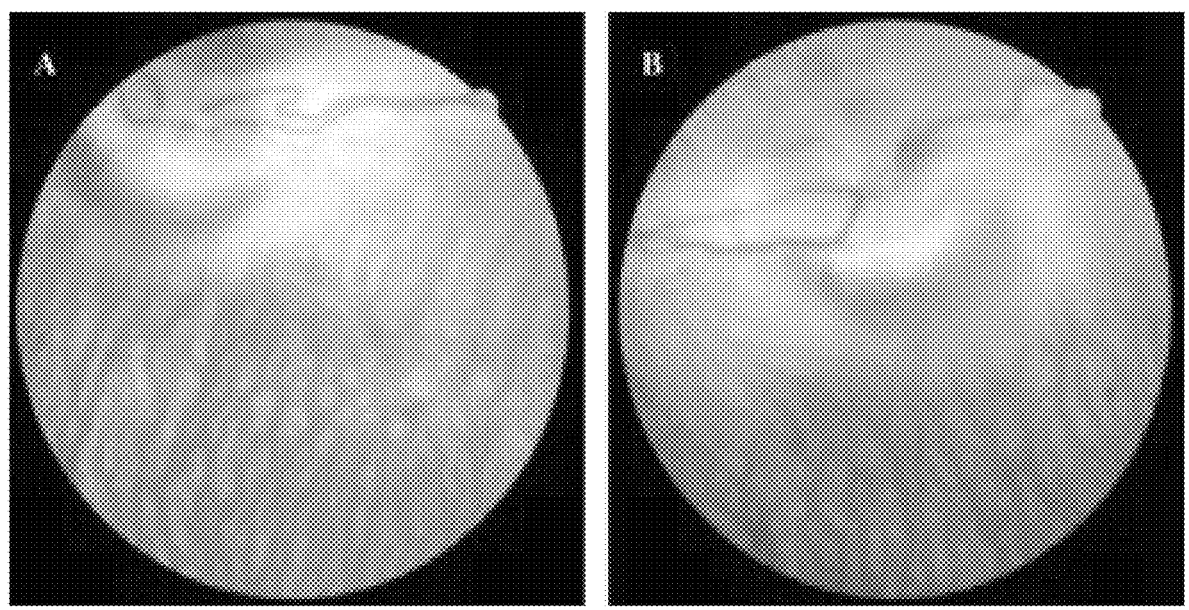
FIG. 6 shows the fundus photographs of the eye of rabbit under vitrectomy lens, wherein A is the group injected with rAAV2/2-ZsGreen (control group), and B is the group injected with rAAV2/2-optimized hOPA1 isoform 2 (experimental group A).

The results were shown in FIG. 6: all rabbits had no obvious complications or damages to the retinal blood vessels and optic nerves, indicating that a normal standard injection into vitreous cavity will not cause obvious inflammatory reactions or other complications.

3. Fluorescence Photography of Retina

Thirty days after vitreous cavity injection, fluorescence photography of retina of the ZsGreen group (control group) showed that GFP was successfully expressed on retina, indicating that rAAV was used as a vector to carry GFP to transfect into the vitreous body of the eye of the rabbit, which demonstrated that rAAV2/2-hOPA1 isoform 2 recombinant gene can be expressed on retina.

4. Immunofluorescence Detection of hOPA1

Thirty days after vitreous cavity injection, the eyeballs of the experimental groups A and B and the control group were peeled off and made into paraffin sections. The paraffin sections were placed in a 65° C. oven to oven-dry for 2 h, subjected to deparaffinization until they were placed in water, and rinsed with PBS three times for 5 min each. The sections were placed in EDTA buffer solution to undergo microwave repair, followed by turning off the power after boiling on medium heat, standing 10 min as an interval, and placing the sections on low heat until boiling. After natural cooling, the sections were washed with PBS 3 times for 5 min each. The sections were placed into 3% hydrogen peroxide solution and incubated at room temperature for 10 min. The sections were washed with PBS 3 times for 5 min each, and blocked with 5% BSA for 20 min after spin-drying. BSA solution was removed, followed by adding 50 μl of diluted primary antibody to each section to cover the tissue and standing overnight at 4° C. Then the sections were washed with PBS three times for 5 min each. The PBS solution was removed, 50 μl-100 μl of fluorescent secondary antibodies of the corresponding species were added to each section, and the sections were incubated away from light at room temperature for 50 min-1 h. The sections were washed with PBS away from light for 3 times, 5 min each time. The PBS solution was removed. 50-100 μl of DAPI was added to each section for staining the nuclei away from light for 5 min. The sections were washed with PBS for 3 times, 5 min each time. After the sections were slightly dried, the sections were mounted with an anti-fluorescence quenching mounting medium, and stored away from light at 4° C. ready for photographing.

Figure 7:
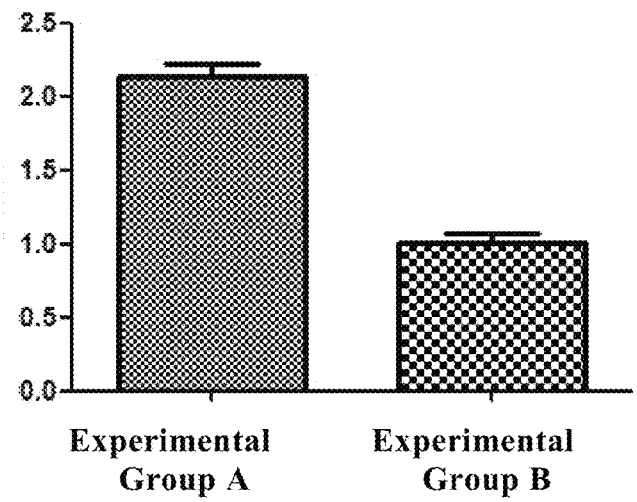
FIG. 7 shows the immunofluorescence detection of eyeball slices of rabbit, in which experimental group A is the group injected with rAAV2/2-optimized hOPA1 isoform 2, and experimental group B is the group injected with rAAV2/2-original hOPA1 isoform 2.

The results of anti-hOPA1 immunofluorescence of retina were shown in FIG. 7, and the fluorescence intensity of the experimental group A was significantly higher than that of the experimental group B, with a significant difference and an increase by more than one fold. It was shown that the expression amount of hOPA1 on the retina of the experimental group A was significantly higher than that of the control group and the experimental group B.

5. OCT Detection

Figure 8:
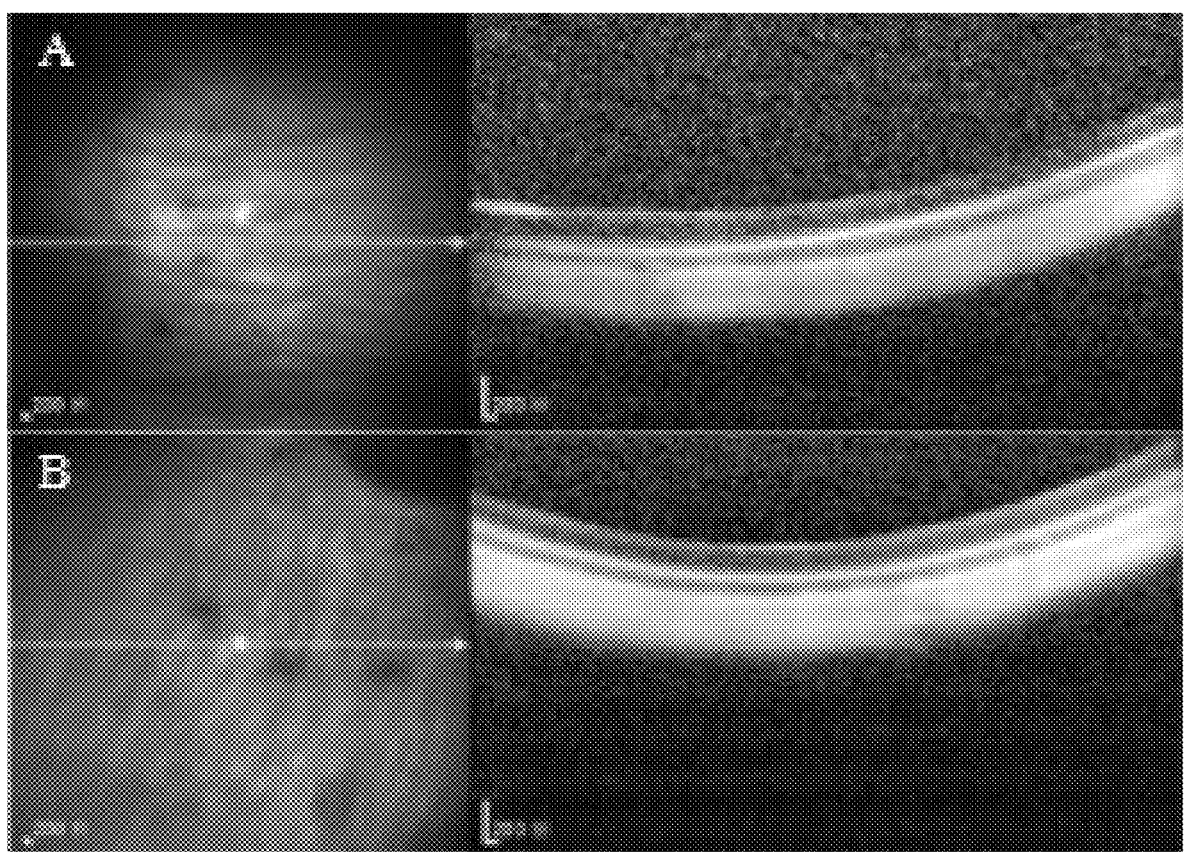
FIG. 8 shows the OCT photographs of the eye of rabbit under vitrectomy lens. Among them, A is the group injected with rAAV2/2-ZsGreen (control group), and B is the group injected with rAAV2/2-optimized hOPA1 isoform 2 (experimental group A).

The results showed that the thickness of the retinal nerve fiber layer of the experimental group A and the experimental group B were 67.55 μm and 66.00 μm, respectively, with no significant difference (P>0.05, FIG. 8).

6. HE Detection

Figure 9:
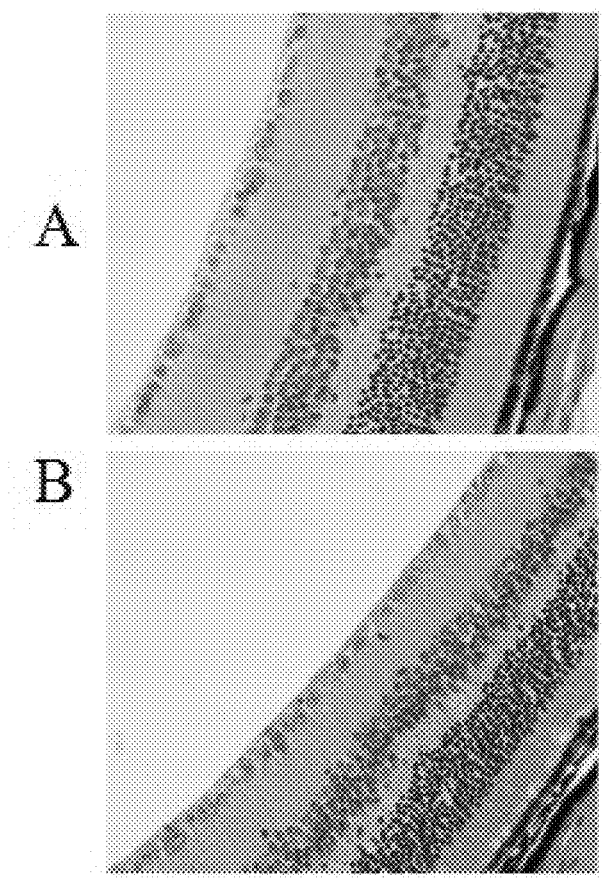
FIG. 9 shows the retina in HE slice of eyeball of rabbit observed under a microscope. Among them, A is the group injected with rAAV2/2-ZsGreen (control group), and B is the group injected with rAAV2/2-optimized hOPA1 isoform 2 (experimental group A).

HE results showed that the number of retinal ganglion cells in the experimental groups and the control group were substantially the same, and the structures were complete, indicating that the rAAV-hOPA1 recombinant gene was safe and did not cause damage to the retina (FIG. 9).

7. Real-Time PCR for Detecting the Expression of hOPA1

Firstly, an NCBI's conserved domain analysis software was used to analyze the conserved structure of hOPA1 to ensure that the amplified fragments with the designed primers were located in the non-conserved region; and then primers were designed using Primer premier 5 according to the primer design principles of fluorescent quantitative PCR:

```
Rabbit-actin-F:
                              (SEQ ID NO.: 6)
ACCTTCTACAACGAGCTGCGC Rabbit-actin-R:
                              (SEQ ID NO.: 7)
TACAGGGACAGCACGGCC Original hOPA1-F:
                              (SEQ ID NO.: 8)
TTAGGTTATTTTGCTGTTGT Original hOPA1-R:
                              (SEQ ID NO.: 9)
TTGTAGTCACTTGGTGTGCC Optimized hOPA1-F:
                              (SEQ ID NO.: 10)
CTGGGCTACTTCGCCGTGGT Optimized hOPA1-R:
                              (SEQ ID NO.: 11)
GGGTGGTCACCTGGTGGGCC
```

1) RNA Extraction and Reverse Transcription

A TRIZOL kit was used to extract total RNA from rabbit retina in different experimental groups and reverse transcription was performed to produce a cDNA template.

2) Fluorescence Quantitative PCR Reaction System and Reaction Procedure

Fluorescent quantitative PCR was performed on the Real-time PCR Detection System. 12.5 µL of SYBR Green mix, 8 µL of ddH2O, 1 µL of each of a pair of primers, 2.5 µL of cDNA sample was added into a 0.2 mL PCR reaction tube, and the total system was 25 µL. Each sample was used for the amplification of the gene of interest and the internal reference gene rabbit-actin, and the amplification of each gene was done in three replicates. When actually adding samples, in order to reduce the error, the reagents which were common in each PCR reaction tube can be added together and then aliquoted. Fluorescent quantitative PCR was performed after completing sample adding.

Amplification was carried out according to the following reaction procedures: total 40 cycles of pre-denaturation at 95° C. for 1 s, denaturation at 94° C. for 15 s, annealing at 55° C. for 15 s, and extension at 72° C. for 45 s, and fluorescence signals were collected during the extension stage of each cycle. The melting curve at 94° C.-55° C. was analyzed after the reaction was completed.

The 2-ΔΔCT relative quantitative method (Livak et al., 2001) was used to study the difference in gene expression amount. This method did not need to make a standard curve; the housekeeping gene rabbit-actin was used as the internal reference gene, and the analysis software that comes with the instrument can automatically generate the expression values.

Figure 10:
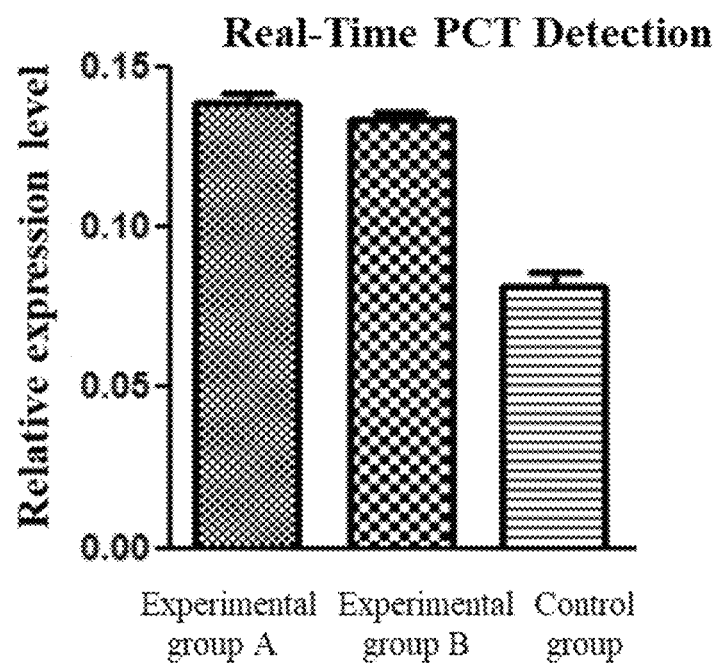
FIG. 10 shows the real-time fluorescent PCR detection results for the relative expression amounts of hOPA1 proteins in the retina of eyeballs of rabbits injected with different plasmids; experimental group A is the group injected with rAAV2/2-optimized hOPA1 isoform 2, experimental group B is the group injected with rAAV2/2-original hOPA1 isoform 2, and the control group is the group injected with rAAV2/2-ZsGreen.

The results were shown in FIG. 10, the relative expression amount of hOPA1 gene mRNA in experimental group A and experimental group B were both higher than the relative expression amount of hOPA1 gene in control group, and the relative expression level of mRNA in experimental group A is slightly higher than that in experimental group B.

8. Western Blot for Detecting hOPA1 Protein Expression

The retinas of eyeballs of rabbits in different experimental groups were peeled off, a RIPA lysis solution of corresponding volumes was added according to 100 µL/50 mg tissues, followed by homogenizing with a homogenizer, and centrifuging to collect the supernatant. After the protein concentration was determined by BCA method, the sample-loading volumes of the experimental groups and the control group were calculated according to the total protein of 50 µg, and SDS-PAGE gel electrophoresis and Western blotting were performed. ECL development was performed after incubating with an antibody.

Figure 11:
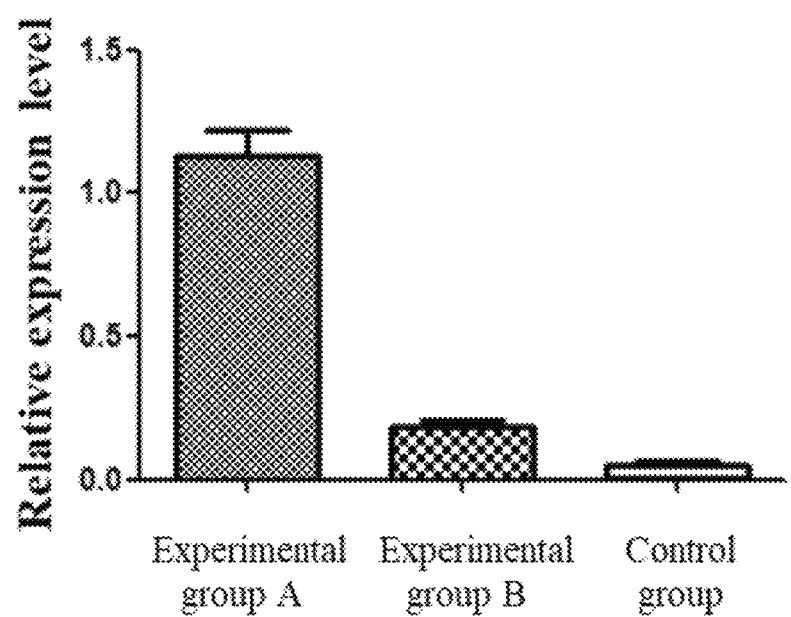
FIG. 11 shows the western blot detection results of hOPA1 proteins in the retina of eyeballs of rabbits injected with different plasmids; experimental group A is the group injected with rAAV2/2-optimized hOPA1 isoform 2, experimental group B is the group injected with rAAV2/2-original hOPA1 isoform 2, and the control group is the group injected with rAAV2/2-ZsGreen.

The results were shown in FIG. 11, the relative expression level of hOPA1 in experimental group A (1.13) by Western blotting was significantly higher than that in experimental group B (0.19) and control group (0.05) with a significant difference $P>0.05$, indicating that the expression level of hOPA1 on retina in experimental group A was significantly increased, which was about 5 times and 22 times higher than that of experimental group B and control group, respectively.

Example 3: Experiment on Long-Term Effects of rAAV2-hOPA1 Recombinant Adeno-Associated Virus on ADOA (Autosomal Dominant Optic Atrophy)

1. Injection into Vitreous Cavity of Eye of Mice

Wild-type C57BL/6J mice were administered via vitreous cavity, and the mice were randomly grouped, 2 mice/cage, administered rAAV2/2-OPA1 at a concentration of 2E11 vg/ml and a volume of 1 µL via sub-vitreous injection. The mice were divided into a 7-day group, a 15-day group, a 20-day group, a 30-day group, a 45-day group, a 60-day group, and a 90-day group after administration. The mice of different groups were sacrificed when the specified date reached, eyeball samples were obtained, and relevant detection and analysis were performed.

2. Real-Time PCR for Detecting the Expression of hOPA1

As the methods and steps described in Example 2, total RNA extraction, RNA concentration determination and electrophoresis identification, reverse transcription and real-time PCR identification were performed.

wherein, the primer sequences used were:

```
Primer F:
                              (SEQ ID NO.: 12)
CTTTAGGTTATTTTGCTGTTGT Primer R:
                              (SEQ ID NO.: 13)
TTGTAGTCACTTGGTGTGCC
```

The reaction conditions used: amplification was performed according to the reaction procedures of 40 cycles of pre-denaturation at 95° C. for 3 min, denaturation at 95° C. for 10 s, annealing at 60° C. for 15 s, and extension at 72° C. for 25 s, and fluorescence signals were collected during the extension stage of each cycle. The melting curve at 95° C.-60° C. was analyzed after the reaction was completed.

The 2-ΔΔCT relative quantitative method (Livak et al., 2001) was used to study the difference in gene expression amount. This method did not need to make a standard curve; the housekeeping gene actin was used as the internal reference gene, and the analysis software that comes with the instrument can automatically generate the expression values.

The results were shown in FIG. 11: after injection using rAAV2-OPA1 virus into the vitreous cavities of the eyes of the mice, all the genes of interest at day 7, day 15, day 20, day 30, day 45, day 60, and day 90 detected by RT-PCR were higher than the level before administration and the expression amount approximately from day 20 to day 30 was the highest.

Example 4: Construction and Identification of Model Mice of ADOA (Autosomal Dominant Optic Atrophy)

Figure 12:
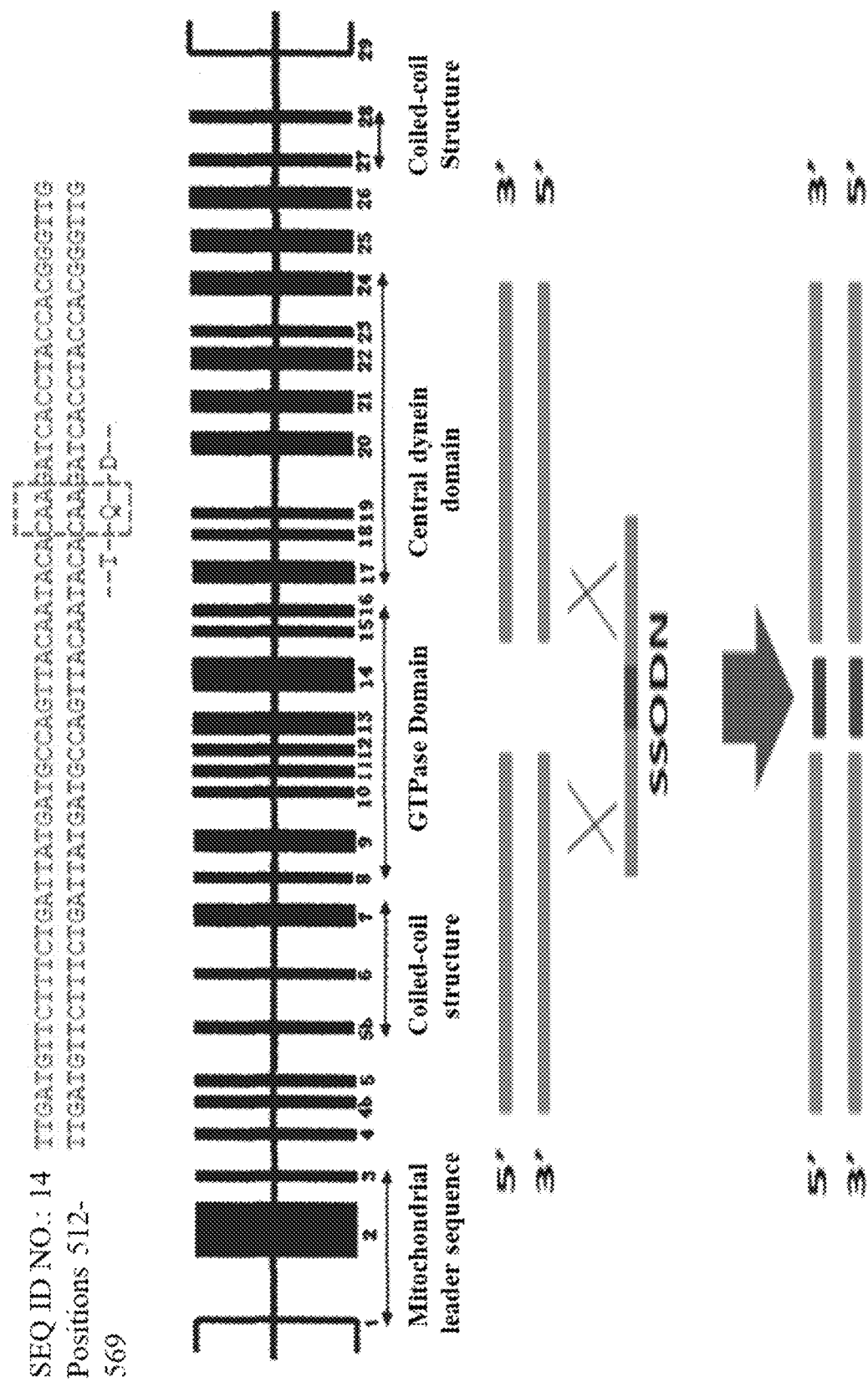
FIG. 12 shows the construction of model mice of ADOA (autosomal dominant optic atrophy).

1. CRISPR/Cas9 technology was utilized to carry out mouse OPA1 Q285Stop point mutation, and the mutated exon was exon8 (highly conserved GTPase region (exons 8-16)). A target ending with NGG was designed at the mutation site and cleaved with the action of CRISPR/Cas9. A donor of about 120 bp was constructed in vitro, and the exogenous donor was inserted into the cleavage site by homologous recombination. The design of guideRNA, the OPA1 structure and the design strategy were shown in FIG. 12.

Among them were: coding region (uppercase), non-coding region (black), and intron region (lowercase);

(SEQ ID NO.: 14)
```
ttgcactgcagccttcccagttcrttaggctgcgtaag
ctctcttgcttgaacactgaccctgaccacttctctactc
tgttccaggctctcacacgccgtgctcccagcctgctc
ttacacgcatgcgctccctgcctaatactccttcccct
tcttctctgttctcacagagcctagtcttggcagagtgt
gatttctctgttagttggtcacctgacagtgtatttga
ctcttatggtgttaatggttaactcattaatgttaatag
gctttctcttttactgtctaactagattatgaaatcct
aaattaataaataaactgaagaagtagcattaattctt
atactagttttactatgaaaacatatagtaagaaaaaa
caatgcaaatttgaatgtatctacatttctcttcatgtat
ctgtggtctttgttttatttcactgacttttgcta
atttaatttttttgcagAAATCTTTGATTGATATGTATT
CTGAAGTTCTTGATGTTCTTTCTGATTATGATGCCA
GTTACAATACACAAGATCACCTACCACGGgtaagggg
aaaatagaccaggacctgctgtcagcaggaaagttcttt
ccttgtgtcatagtaatttctgtatttcccatgatacctc
agatacaaagcattgcttcgttccttattttggagac
cataaaagcaaatatatatgttttggaagaaaaatgtca
gatatttgccattatacattcattatagtgttaaaata
cctaggcaaaaactgtaaacgtttggatgaaatttagt
ctaacagaatccaaaagtatgtttgtaaaatgtaaactg
gttatggaaaatatttgtggaaagttaatgatctggttt
tagaaataactttcaattggcatagttttcaaaacaaa
aatttgaatgtaaatagtggagccaattaattctttg
ctatatgtatctccagagtacctacatgcatcaaacttc
attctttcaaaaaaaaagaaaacaaacaaacaaacac
tttttttggctctaaatatcttaaaatatgttttaaatg
ataacattcaaaccctacatacatttaatttggtatgac
aagagaactaatgtatgctccttgtcttgtgatag
```

OPA1 (Q285*)-sgRNA1:
(SEQ ID NO.: 15)
<u>ATACACAAGATCACCTACCA</u>CGG

OPA1 (Q285*)-sgRNA2:
(SEQ ID NO.: 16)
CCA<u>GTTACAATACACAAGATCAC</u>

OPA1 (Q285*)-120bp oligo:
(SEQ ID NO.: 17)
```
TTGATATGTATTCTGAAGTTCTTGATGTTCTTTCTGAT
TATGATGCCAGTTACAATACATAAGATCACCT
ACCACGGgtaaggggaaaatagaccaggacctgctgtca
gcaggaaagtt
```

2. Construction of Model Mice of ADOA (Autosomal Dominant Optic Atrophy)

(1) a CRISPR-CAS9 technology was used to construct a recombinant plasmid having OPAL Q285Stop point mutation, followed by replacing with a DNA sequence having a selectable marker for homologous mutation to obtain a monoclonal embryonic stem cell having a positive Q285Stop OPA1 point mutation;

(2) chimeric mice were prepared by using the mouse embryonic stem cell clone having an OPA1 point mutation obtained in step (1);

(3) the chimeric mice obtained in step (2) were allowed to mate with normal wild-type mice and then breeding, and the offspring were screened for heterozygous mice having the OPA1 point mutation;

(4) a homozygous mouse having OPA1 Q(glutamine) 285Stop point mutation was obtained through the mutual mating of the heterozygous mice obtained in step (3), thereby obtaining a mouse model of OPA1 Q(glutamine) 285Stop point mutation.

3. Identification of Model Mice of Point Mutation of ADOA (Autosomal Dominant Optic Atrophy)

3.1 Genomic DNA Extraction (1) Digestion: a mouse toe of 0.5 cm was cut from a mouse within a week after birth and added in a 1.5 ml EP tube, and subjected to a slight centrifugation, followed by adding 500 μl of lysis solution (formulation: 100 mM Tris pH 8.0, 5 mM EDTA pH 8.0, 0.5% SDS, NaCl 1.17 g/100 ml), 0.5 μl proteinase K (concentration: 20 mg/ml, dissolved in 20 mM Tris pH 7.4 and 1 mM $CaCl_2$), 50% glycerol buffer, stored at −20° C.), mixing evenly and digesting in a water bath at 55° C. overnight;

(2) DNA extraction via isopropanol precipitation:

1) The centrifuge tube was taken from the water bath kettle and allowed standing at room temperature for 10-15 min to lower the sample temperature to room temperature, and the centrifuge tube was inverted to mix evenly. Centrifugation was performed at 13,000 rpm at room temperature for 15 min.

2) 400 μl of supernatant was pipetted into another new centrifuge tube. An equal volume of isopropanol was added and the tube was immediately turned upside down gently to mix thoroughly; when a white flocculent precipitate appeared, centrifugation was performed at 12000 rpm at room temperature for 10 min and the supernatant was discarded.

3) 700 μl of ice-cold 75% ethanol was added to the centrifuge tube to rinse the product, and the tube was turned upside down gently to mix evenly. Centrifugation was performed at 12000 rpm at room temperature for 5 min and all the supernatant was discarded.

4) The centrifuge tube was turned upside down on an absorbent paper to absorb the ethanol. After air-drying, DNA was dissolved in 50 μl of sterile ddH2O, dissolution was allowed at 55° C. for 2 h (if not used immediately, stored at −20° C.).

5) The concentration of DNA was determined and 100-200 ng of DNA was taken out and used as PCR template.

3.2 Primers and PCR reaction A primer pair was synthesized so as to obtain a nucleic acid amplification product (length of 530 bp) containing Q285 site through PCR amplification.

3.3 Identification Results

The total DNA of the mice was extracted and the PCR products were sequenced.

Figure 13:
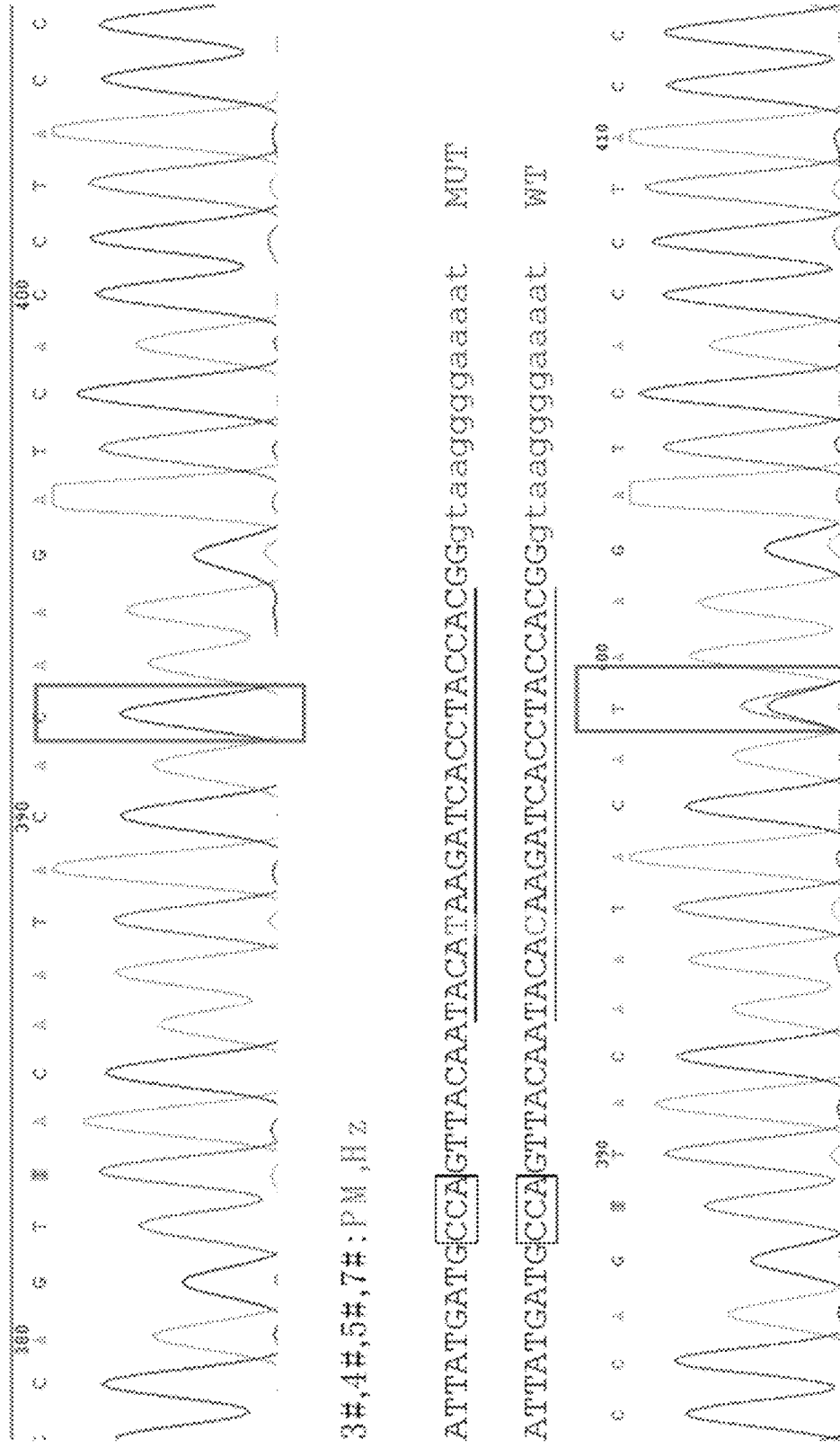
FIG. 13 shows the genotype identification of model mice of point mutation of ADOA (autosomal dominant optic atrophy). The polynucleotide sequences shown in the figure include MUT (SEQ ID NO: 18) and WT (SEQ ID NO: 19).

The results were shown in FIG. 13, which showed that the base C at position 285 has mutated into T, indicating that the point mutant mouse was successfully prepared.

Example 5: Experiment on Improvement of Model Mice of Point Mutation of ADOA (Autosomal Dominant Optic Atrophy) with rAAV2-hOPA1 Recombinant Adeno-Associated Virus 1. Method OPA1 mutant mice of 2 mice/cage were taken and divided into 3 groups. The rAAV-OPA1 concentration was 2E11 vg/ml and the administration volume was 1 μL, and the mice were injected subvitreously. The mice in different groups were sacrificed after one month and three months to obtain eyeball samples. The OPA mutant group was injected subvitreously with 1 μL of PBS, and the wild mice of 2 mice/cage were taken and were injected subvitreously with 1 μL of PBS as the control group. Detection and analysis were carried out for the changes of ATP content and mitochondrial morphology observation.

2. Changes of ATP Content in the Retina of Mice after Administration by High Performance Liquid Chromatography (HPLC)

2.1 the Retina of Wild-Type Mice and OPA1 Mutant Mice after Administration was Taken and Washed Once with Pre-Cooled PBS, and Placed in Liquid Nitrogen 2.2 ATP Extraction (1) Liquid nitrogen grinding (2) 1 ml of iced phenol-TE (containing DTT), 200 μl of chloroform and 150 μl of ultrapure water were added, followed by shaking and mixing evenly at 4° C. for 20 s, and performing centrifugation at 10,000 g for 10 min (3) 200 μl of water phase was taken, filtered with 0.22 μm filter membrane, and loaded onto a machine to detect ATP by HPLC (4) Protein concentration was determined using BCA method 2.3 Chromatographic Analysis Method Chromatographic column: Sepax GP-C18, (4.6 mm×250 mm, 5 μm)

Mobile phase A: 15 mM KH2PO4, 15 mM KCL, and 0.1 M KOH used to adjust the pH to 6.0

Mobile phase B: 85% mobile phase A mixed with 15% acetonitrile

Loading volume: 20 μl

Detection wavelength: 254 nm

Gradient elution conditions:

| Time (min) | Mobile phase A (%) | Mobile phase B (%) | Flow rate |
|---|---|---|---|
| 0 | 100 | 0 | 0.54 ml/min |
| 0.28 | 97 | 3 | 0.54 ml/min |
| 9.72 | 91 | 9 | 0.54 ml/min |
| 13.89 | 0 | 100 | 0.54 ml/min |
| 19.44 | 0 | 100 | 0.54 ml/min |
| 33 | 100 | 0 | 0.54 ml/min |
| 44 | 100 | 0 | 0.54 ml/min |

Figure 14:
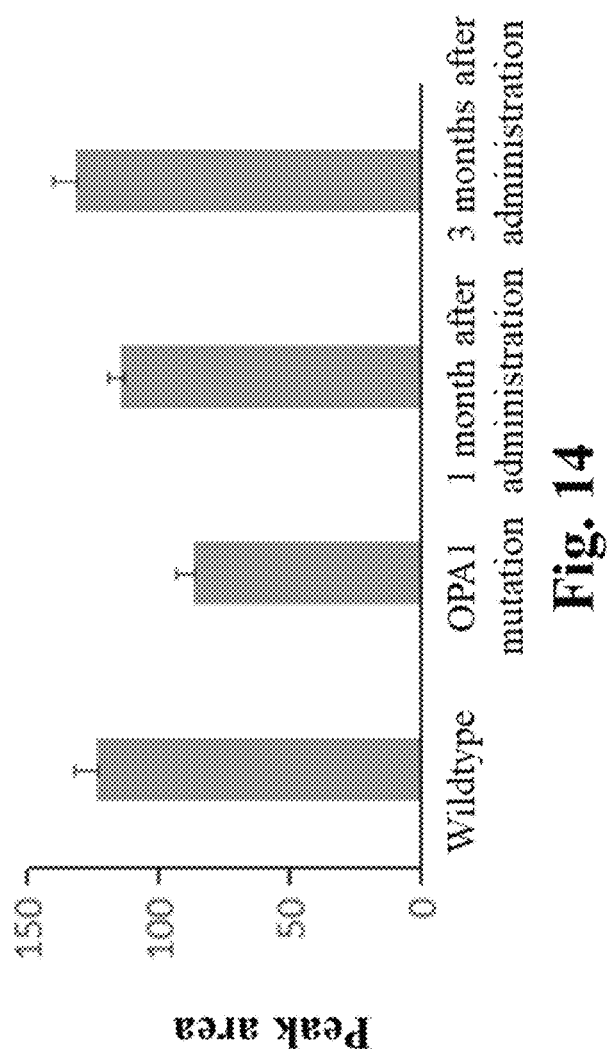
FIG. 14 shows the changes of ATP content in the retina of mice after administration detected by high performance liquid chromatography (HPLC).

The results were shown in FIG. 14: HPLC detection found that the ATP content in the OPA1 mutant mice in the control group was decreased, while in the experimental group that the rAAV2-OPA1 viruses were injected into the vitreous cavities of the eyeballs of the mice, the content increased to a normal level after administration, indicating that the ATP content can be restored after OPA1 administration.

It can be seen from FIG. 14 that after 1 month of administration and 3 months of administration, the ATP content in the eyeballs of the mice increased with time; the ATP content in the eyeballs of the OPA1 mutant mice until 3 months after administration was equivalent to the ATP content in the eyeballs of the wild-type mice, suggesting that the use of rAAV2-OPA1 virus effectively reversed the occurrence of the disease.

3. Observation of Morphology of Mitochondria by Transmission Electron Microscope (TEM)

After the mouse eyeballs were taken, they were respectively immersed in 2.5% glutaraldehyde, fixed overnight, washed with 0.1 mol/L phosphate buffer solution 3 times for 15 min each time, fixed with osmic acid for 2 h, and washed with 0.1 mol/L phosphate buffer solution 3 times for 15 min each time, and gradient dehydration was carried out using ethanol (50%, 70%, 80%, 90%, 100%), followed by transiting to use pure acetone and dehydrating with pure acetone twice. Each step lasted 15 minutes. Gradient penetration was carried out using 812 resin:acetone with the ratios of 3:1, 3:2, and 3:3 with each step lasting 40 minutes, followed by embedding with a pure embedding agent at 45° C. overnight, polymerizing at 60° C., sectioning, staining, and observing under a transmission electron microscope.

Figure 15:
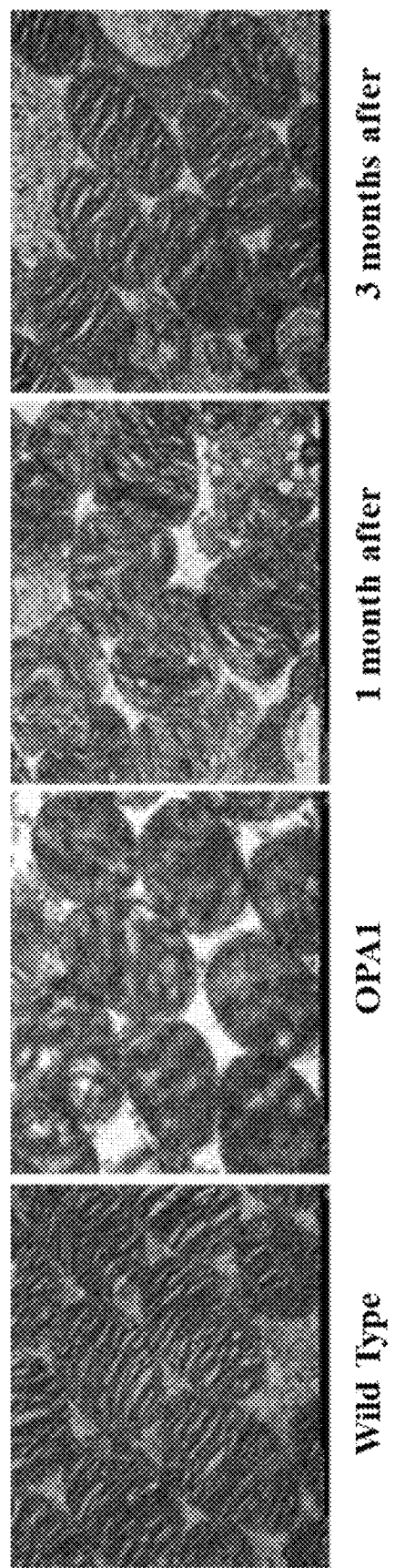
FIG. 15 shows the morphology of mitochondria observed by transmission electron microscope (TEM).

The results were shown in FIG. 15, TEM electron microscopy observed the disappearance of mitochondrial cristae in OPA1 mutant mice, indicating the occurrence of apoptosis. The recovery of mitochondrial cristae in OPA1 mutant mice was observed 1 month after administration, and significant recovery was observed after 3 months, suggesting that the use of rAAV2-OPA1 virus effectively reversed the occurrence of the disease.

Discussion

With the rapid development of gene therapy in the treatment of eye diseases, the cure of ADOA will not be difficult. Since human eyes and rabbit eyes are similar in anatomy and volume, the present invention used rabbit eye as a model for vitreous cavity injection of rAAV2/2-hOPA1 isoform 2. This experiment studied the injection dosage, safety level and postoperative complications, and provided important references for future clinical trials. All rabbits were subjected to slit lamp and intraocular pressure examinations, and had no obvious abnormalities, no conjunctival congestion and secretions, no endophthalmitis, and no increase in intraocular pressure. Fundus photographs taken one month after the operation showed that all rabbits had no obvious complications or damages to the retinal blood vessels and optic nerves, suggesting that this experiment was safe.

The results of immunofluorescence, real-time quantitative PCR and Western blot could demonstrate that hOPA1 can be stably expressed on the retina of the rabbits. Since ADOA lesions can cause the apoptosis of retinal ganglion cells around the optic disc, a stable fluorescence expression in the retina around the optic disc can be detected in the retinal sections in the rAAV-ZsGreen group. The fluorescent staining results of hOPA1 could demonstrate that it can reach the retinal ganglion cells, indicating that rAAV2/2-hOPA1 isoform 2 can reach the diseased area in the patient's eye. The results of fundus photography and OCT showed that a single vitreous cavity injection of $5\times10^{10}$ vg/mL rAAV2/2-hOPA1 isoform 2 was safe and had no retinal toxicity, and could be used in future clinical trials.

All the documents referred in the present invention are incorporated by reference in the present application as if each document was individually incorporated by reference. In addition, it should be understood that after reading the teachings of the present invention described above, a skilled person in the art can make various changes or modifications to the present invention, and these equivalent forms also fall into the scope as defined by the appended claims of the present application.

The invention claimed is:

1. A recombinant nucleic acid, comprising a nucleotide sequence that encodes a human type II mitochondrial dynein-like GTPase, and wherein the nucleotide sequence is ≥95% identical to the sequence of SEQ ID NO: 1.

2. The recombinant nucleic acid of claim 1, wherein the nucleotide sequence is ≥98% identical to the sequence of SEQ ID NO: 1.

3. The recombinant nucleic acid of claim 1, wherein the nucleotide sequence is identical to the sequence of SEQ ID NO: 1.

4. The recombinant nucleic acid of claim 1, further comprising an untranslated region (UTR) sequence, a promoter sequence, or both.

5. The recombinant nucleic acid of claim 4, wherein the UTR sequence is a 5'-UTR sequence, a 3'-UTR sequence, or both.

6. The recombinant nucleic acid of claim 5, wherein the 5'-UTR sequence is operably linked to the 5'-end of the nucleotide sequence.

7. The recombinant nucleic acid of claim 5, wherein the 3'-UTR sequence is operably linked to the 3'-end of the nucleotide sequence.

8. The recombinant nucleic acid of claim 5, comprising the 5'-UTR sequence operably linked to the 5'-end of the nucleotide sequence and the 3'-UTR sequence operably linked to the 3'-end of the nucleotide sequence.

9. The recombinant nucleic acid of claim 5, wherein the recombinant nucleic acid has a structure of formula I from the 5'-end to the 3'-end:

$$Z1-Z2-Z3 \quad (I)$$

wherein each "-" is independently a bond or a nucleotide linker sequence;

Z1 is null or a 5'-UTR sequence;

Z2 is the nucleotide sequence encoding the human type II mitochondrial dynein-like GTPase; and Z3 is a 3'-UTR sequence.

10. A vector, comprising the recombinant nucleic acid of claim 1.

11. The vector of claim 10, wherein the vector is a DNA virus vector or a retroviral vector.

12. The vector of claim 10, wherein the vector is a plasmid or viral vector.

13. The vector of claim 12, wherein the viral vector is selected from a lentiviral vector, an adenovirus vector, an adeno-associated virus (AAV) vector, and a combination thereof.

14. The vector of claim 13, wherein the vector is the AAV vector.

15. The vector of claim 14, wherein the AAV vector has a serotype selected from AAV2, AAV5, AAV7, AAV8, and a combination thereof.

16. An isolated host cell, comprising the recombinant nucleic acid of claim 1, and wherein the nucleotide sequence is integrated into a chromosome of the isolated host cell.

17. The isolated host cell of claim 16, wherein the isolated host cell is selected from the group consisting of a 293T cell, a photoreceptor cell, a visual cell, and a nerve cell.

18. A pharmaceutical composition, comprising (a) an adeno-associated virus comprising the recombinant nucleic acid of claim 1; and (b) a pharmaceutically acceptable carrier or excipient.

19. The pharmaceutical composition of claim 18, wherein a dosage form of the pharmaceutical composition is selected from the group consisting of a lyophilized composition, and a liquid composition.

20. The pharmaceutical composition of claim 18, wherein a concentration of the virus in the pharmaceutical composition is $1 \times 10^9$-$1 \times 10^{16}$ viruses/mL.

21. The pharmaceutical composition of claim 20, wherein the concentration is $2 \times 10^{11}$-$1 \times 10^{12}$ viruses/mL.

22. A method for increasing the expression and/or activity of a mitochondrial dynein-like GTPase in a cell, comprising: contacting the cell with a pharmaceutical composition comprising (a) a vector, comprising a recombinant nucleic acid, wherein the recombinant nucleic acid comprises a nucleotide sequence that encodes a human type II mitochondrial dynein-like GTPase, and wherein the nucleotide sequence is 95% identical to the sequence of SEQ ID NO: 1; and (b) a pharmaceutically acceptable carrier or excipient.

23. A method for treating an eye disease, comprising: administering a therapeutically acceptable amount of pharmaceutical composition to the eye of a subject in need thereof, wherein the pharmaceutical composition comprises (a) an adeno-associated virus comprising a recombinant nucleic acid, wherein the recombinant nucleic acid comprises a nucleotide sequence that encodes a human type II mitochondrial dynein-like GTPase, and wherein the nucleotide sequence is ≥95% identical to the sequence of SEQ ID NO: 1; and (b) a pharmaceutically acceptable carrier or excipient wherein the eye disease is autosomal dominant optic atrophy (ADOA) resulting from haploinsufficiency of Optic Atrophy 1 (OPA1).

24. A method for preparing a recombinant nucleic acid, comprising culturing a host cell comprising the recombinant nucleic acid, wherein the recombinant nucleic acid comprises a nucleotide sequence that encodes a human type II mitochondrial dynein-like GTPase, and wherein the nucleotide sequence is ≥95% identical to the sequence of SEQ ID NO: 1, thereby obtaining the recombinant nucleic acid.

* * * * *

UNITED STATES PATENT AND TRADEMARK OFFICE
CERTIFICATE OF CORRECTION

PATENT NO. : 11,459,584 B2
APPLICATION NO. : 17/182903
DATED : October 4, 2022
INVENTOR(S) : Bin Li It is certified that error appears in the above-identified patent and that said Letters Patent is hereby corrected as shown below:

In the Claims

At Column 48, Claim 22, Line 29-37:
"22. A method for increasing the expression and/or activity of a mitochondrial dynein-like GTPase in a cell, comprising: contacting the cell with a pharmaceutical composition comprising (a) a vector, comprising a recombinant nucleic acid, wherein the recombinant nucleic acid comprises a nucleotide sequence that encodes a human type II mitochondrial dynein-like GTPase, and wherein the nucleotide sequence is 95% identical to the sequence of SEQ ID NO: 1; and (b) a pharmaceutically acceptable carrier or excipient."

Should be changed to:
--22. A method for increasing the expression and/or activity of a mitochondrial dynein-like GTPase in a cell, comprising: contacting the cell with a pharmaceutical composition comprising (a) a vector, comprising a recombinant nucleic acid, wherein the recombinant nucleic acid comprises a nucleotide sequence that encodes a human type II mitochondrial dynein-like GTPase, and wherein the nucleotide sequence is ≥ 95% identical to the sequence of SEQ ID NO: 1; and (b) a pharmaceutically acceptable carrier or excipient.--

Signed and Sealed this
Third Day of January, 2023

Katherine Kelly Vidal
*Director of the United States Patent and Trademark Office*